(12) United States Patent
De Windt et al.

(10) Patent No.: US 8,383,603 B2
(45) Date of Patent: Feb. 26, 2013

(54) MEANS AND METHODS FOR COUNTERACTING, DELAYING AND/OR PREVENTING HEART DISEASE

(75) Inventors: Leon Johannes De Windt, Culemborg (NL); Paula Alexandra Da Costa Martins, Baarlo (NL)

(73) Assignees: Universiteit Maastricht, Maastricht (NL); Academisch Ziekehuis Maastricht, Maastricht (NL)

( * ) Notice: Subject to any disclaimer, the term of this patent is extended or adjusted under 35 U.S.C. 154(b) by 23 days.

(21) Appl. No.: 12/737,213

(22) PCT Filed: Jun. 16, 2009

(86) PCT No.: PCT/NL2009/050345
§ 371 (c)(1),
(2), (4) Date: Jan. 7, 2011

(87) PCT Pub. No.: WO2010/005295
PCT Pub. Date: Jan. 14, 2010

(65) Prior Publication Data
US 2011/0110902 A1 May 12, 2011

(30) Foreign Application Priority Data
Jun. 16, 2008 (EP) .................................. 08158359

(51) Int. Cl.
*C12N 15/11* (2006.01)
*C07H 21/02* (2006.01)
*C07H 21/04* (2006.01)
*C12Q 1/68* (2006.01)

(52) U.S. Cl. .................... 514/44 A; 536/23.1; 536/24.5; 435/6.1

(58) Field of Classification Search ........................ None
See application file for complete search history.

(56) References Cited

U.S. PATENT DOCUMENTS

2009/0239818 A1* 9/2009 Cheng .............................. 514/52

FOREIGN PATENT DOCUMENTS

| WO | WO 2008/043521 A2 | 4/2008 |
| WO | WO 2010/005295 A1 | 1/2010 |

OTHER PUBLICATIONS

Arron, et al.; NFAT dysregulation by increased dosage of DSCR1 and DYRK1A on chromosome 21; Nature; vol. 443; Jun. 1, 2006; 595-600.
Chien, Kenneth R.; MicroRNAs and the tell-tale heart; Nature; vol. 447; May 24, 2007; 389-390.
Heineke, et al.; Regulation of cardiac hypertrophy by intracellular signaling pathways; Nature Review; vol. 7; Aug. 2006; 589-600.
International Search Report PCT/NL2009/050345 dated Oct. 30, 2009.
Saved, et al.: MicroRNAs Play an Essential Role in the Development of Cardiac Hypertrophy; American Heart Association Journal; 2007: 100: 416-424.
Thum, et al., MicroRNAs in the Human Heart a Clue to Fetal Gene Reprogramming in Heart Failure; American Heart Association Journal; 2007; 116: 258-267.
PCT International Preliminary Report on Patentability, PCT/NL2009/050345 dated Dec. 18, 2010.

*Primary Examiner* — Doug Schultz
(74) *Attorney, Agent, or Firm* — TraskBritt

(57) ABSTRACT

The invention relates to the fields of molecular biology and medicine, more specifically to treatment and prevention of heart disease. The invention provides alternative methods for counteracting, diminishing, treating, delaying and/or preventing heart disease.

32 Claims, 7 Drawing Sheets

SEQUENCE LISTING

```
<160> NUMBER OF SEQ ID NOS: 13

<210> SEQ ID NO 1
<211> LENGTH: 20
<212> TYPE: RNA
<213> ORGANISM: Artificial
<220> FEATURE:
<223> OTHER INFORMATION: antisense miR-199b

<400> SEQUENCE: 1
gaacagguag ucuaaacacu                                                     20

<210> SEQ ID NO 2
<211> LENGTH: 23
<212> TYPE: RNA
<213> ORGANISM: Artificial
<220> FEATURE:
<223> OTHER INFORMATION: hsa-miR-199b-5p

<400> SEQUENCE: 2
cccaguguuu agacuaucug uuc                                                 23

<210> SEQ ID NO 3
<211> LENGTH: 22
<212> TYPE: RNA
<213> ORGANISM: Artificial
<220> FEATURE:
<223> OTHER INFORMATION: hsa-miR-199b-3p

<400> SEQUENCE: 3
acaguagucu gcacauuggu ua                                                  22

<210> SEQ ID NO 4
<211> LENGTH: 49
<212> TYPE: RNA
<213> ORGANISM: Mus musculus

<400> SEQUENCE: 4
ccagaggaua ccuccacucc gucuacccag uguuuagacu accuguuca                     49

<210> SEQ ID NO 5
<211> LENGTH: 22
<212> TYPE: RNA
<213> ORGANISM: Homo sapiens

<400> SEQUENCE: 5
```

```
ccaguguuua gacuaucugu uc                                           22

<210> SEQ ID NO 6
<211> LENGTH: 9
<212> TYPE: RNA
<213> ORGANISM: Artificial
<220> FEATURE:
<223> OTHER INFORMATION: 3' part of hsa-miR-199b

<400> SEQUENCE: 6 cuaucagau                                                           9

<210> SEQ ID NO 7
<211> LENGTH: 9
<212> TYPE: RNA
<213> ORGANISM: Artificial
<220> FEATURE:
<223> OTHER INFORMATION: 5' part of hsa-miR-199b

<400> SEQUENCE: 7 uugugaccc                                                           9

<210> SEQ ID NO 8
<211> LENGTH: 10
<212> TYPE: RNA
<213> ORGANISM: Mus musculus

<400> SEQUENCE: 8
gaagggaaag                                                         10

<210> SEQ ID NO 9
<211> LENGTH: 10
<212> TYPE: RNA
<213> ORGANISM: Mus musculus

<400> SEQUENCE: 9
ggacacugga                                                         10

<210> SEQ ID NO 10
<211> LENGTH: 10
<212> TYPE: RNA
<213> ORGANISM: Mus musculus

<400> SEQUENCE: 10
gaagguaaag                                                         10

<210> SEQ ID NO 11
<211> LENGTH: 10
<212> TYPE: RNA
<213> ORGANISM: Mus musculus

<400> SEQUENCE: 11
ggacacugga                                                         10

<210> SEQ ID NO 12
<211> LENGTH: 10
<212> TYPE: RNA
<213> ORGANISM: Mus musculus

<400> SEQUENCE: 12
ggagagugga                                                         10

<210> SEQ ID NO 13
<211> LENGTH: 24
<212> TYPE: DNA
```

```
<213> ORGANISM: Artificial
<220> FEATURE:
<223> OTHER INFORMATION: antagomir
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: 2-O-methyl adenosine
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (21)..(23)
<223> OTHER INFORMATION: gm
<220> FEATURE:
<221> NAME/KEY: modified_base
<222> LOCATION: (24)..(24)
<223> OTHER INFORMATION: cholesterol modified

<400> SEQUENCE: 13
gaacagguag ucuaaacacu gggt                                          24
```

MEANS AND METHODS FOR COUNTERACTING, DELAYING AND/OR PREVENTING HEART DISEASE

CROSS-REFERENCE TO RELATED APPLICATIONS

This is a national phase entry under 35 U.S.C. §371 of International Patent Application PCT/NL2009/050345, filed Jun. 16, 2009, published in English as International Patent Publication WO 2010/005295 A1 on Jan. 14, 2010, which claims the benefit under Article 8 of the Patent Cooperation Treaty to European Patent Application Serial No. 08158359.3, filed Jun. 16, 2008, the entire disclosure of each of which is hereby incorporated herein by this reference.

TECHNICAL FIELD

The invention relates to the fields of molecular biology and medicine, more specifically to treatment, delay and prevention of heart disease.

BACKGROUND

Heart disease, also called cardiovascular disease is a broad term used to describe a range of diseases that affect the heart and/or blood vessels. The conditions include coronary artery disease, heart attack, high blood pressure, stroke and heart failure. Cardiovascular disease is the No. 1 worldwide killer of men and women, e.g., in the U.S. it is responsible for 40 percent of all deaths, more than all forms of cancer combined.

A common form of cardiovascular disease is coronary artery disease, which affects the arteries that supply the heart muscle with blood. Sometimes known as CAD, coronary artery disease is the leading cause of heart attacks. It generally means that blood flow through the coronary arteries has become obstructed, reducing blood flow to the heart muscle. The most common cause of such obstructions is a condition called atherosclerosis, a largely preventable type of vascular disease. Coronary artery disease and the resulting reduced blood flow to the heart muscle can lead to other heart problems, such as chest pain (angina) and heart attack (myocardial infarction).

A heart attack is an injury to the heart muscle caused by a loss of blood supply. The medical term for heart attack is "myocardial infarction," often abbreviated MI. A heart attack usually occurs when a blood clot blocks the flow of blood through a coronary artery—a blood vessel that feeds blood to a part of the heart muscle. Interrupted blood flow to a heart can damage or destroy a part of the heart muscle.

A heart disease that affects the heart muscle itself is called a cardiomyopathy. Some types of cardiomyopathy are genetic, while others occur for reasons that are less well understood. Types of cardiomyopathy include ischemic, which is caused by loss of heart muscle from reduced coronary blood flow; dilated, which means the heart chambers are enlarged; hypertrophic, which means the heart muscle is thickened; and idiopathic, which means the cause is unknown. One of the most common types of cardiomyopathy is idiopathic dilated cardiomyopathy—an enlarged heart without a known cause.

Heart disease can be either acquired (later in life) or congenital. Congenital heart disease refers to a form of heart disease that develops before birth (congenital). Congenital heart disease is a broad term and includes a wide range of diseases and conditions. These diseases can affect the formation of the heart muscle or its chambers or valves. They include such conditions as narrowing of a section of the aorta (coarctation) or holes in the heart (atrial or ventricular septal defect). Some congenital heart defects may be apparent at birth, while others may not be detected until later in life.

Next to the heart muscle itself, heart disease can also affect other structure, such as the heart valves. Four valves within the heart keep blood flowing in the right direction. Valves may be damaged by a variety of conditions leading to narrowing (stenosis), leaking (regurgitation or insufficiency) or improper closing (prolapse). Valvular disease may either be congenital, or the valves may be damaged by such conditions as rheumatic fever, infections (infectious endocarditis), connective tissue disorders, and certain medications or radiation treatments for cancer.

Heart rhythm problems (arrhythmias) occur when the electrical impulses in a heart that coordinate heartbeats do not function properly, causing the heart to beat too fast, too slow or irregularly. Other forms of cardiovascular disease can indirectly cause arrhythmias.

Perhaps the most common form of cardiovascular disease in the Western world, affecting about one in four Americans is high blood pressure (hypertension), which means that the blood is pumped with excessive force through the blood vessels. Although potentially life-threatening, it is one of the most preventable and treatable types of cardiovascular disease. High blood pressure also causes many other types of cardiovascular disease, such as stroke and heart failure.

Heart failure, a progressive disorder in which damage to the heart causes weakening of the cardiovascular system can result from any of the before mentioned structural or functional cardiac disorders. It manifests by fluid congestion or inadequate blood flow to tissues as a result of the heart's inability to fill with or pump a sufficient amount of blood through the body.

Depending on the side of the heart affected, the symptoms can be diverse and diagnosis is impossible on symptoms alone. Left sided heart failure results in congestion of the lung veins and symptoms that reflect this, as well as poor circulation to the body, whereas right sided heart failure presents with, e.g., peripheral edema and nocturia.

Heart failure may result from one or the sum of many causes. Many affect both sides, such as ischemic heart disease, chronic arrhythmias, cardiomyopathy, cardiac fibrosis, chronic severe anemia, and thyroid disease, whereas others, such as hypertension, aortic and mitral valve disease and coarctation preferably cause left-sided heart failure and pulmonary hypertension and pulmonary or tricuspid valve disease often result in right-sided heart failure.

These causes of heart failure have in common that they all reduce the efficiency of the myocardium, or heart muscle, through damage or overloading. Over time, the resulting increase in workload will produce changes to the heart itself, which, for instance, include reduced contractility, a reduced stroke volume, reduced spare capacity, increased heart rate, hypertrophy of the myocardium and/or enlargement of the ventricles. These changes of the heart result in reduced cardiac output and increased strain on the heart, which increases the risk of cardiac arrest and reduces blood supply to the rest of the body.

Current treatment of heart failure focuses on treating the symptoms and signs and preventing the progression of the disease. Treatment includes exercise, eating healthy foods, reduction in salty foods, and abstinence from smoking and drinking alcohol. Further, pharmacological management can be applied focused on relieving symptoms, maintaining a euvolemic state, and delaying progression of heart failure.

Drugs used include: diuretic agents, vasodilator agents, positive inotropes, ACE inhibitors, beta blockers, and aldosterone antagonists.

Heart failure is a serious disorder that carries a reduced life expectancy. Many forms of heart failure can be controlled with medication, lifestyle change, and correction of any underlying disorder. However, heart failure is usually a chronic illness, and it may worsen with infection or other physical stressors. There is no real cure for heart failure.

Therefore, there is an unmet need for alternative treatments for heart failure and heart disease in general.

DISCLOSURE

An object of the present invention is to provide an alternative treatment for, and/or at least partial prevention of, heart disease.

Accordingly, the present invention provides alternative means and methods for counteracting, diminishing, treating, delaying and/or preventing heart disease.

In one embodiment, the invention provides a method for diminishing, counteracting, treating, delaying and/or preventing heart disease, comprising counteracting the expression, amount and/or activity of microRNA in a cell.

MicroRNAs (miRNAs) are small RNA molecules encoded in the genomes of plants and animals. These highly conserved, ~21-mer RNAs usually regulate the expression of genes by binding to the 3'-untranslated regions (3'-UTRs) of specific mRNAs. Each miRNA is thought to regulate multiple genes, and since hundreds of miRNA genes are predicted to be present in higher eukaryotes the potential regulatory circuitry afforded by miRNA is enormous. Several research groups have provided evidence that miRNAs may act as key regulators of processes as diverse as early development, cell proliferation and cell death, apoptosis and fat metabolism, and cell differentiation. Recent studies of miRNA expression implicate miRNAs in brain development, chronic lymphocytic leukemia, colonic adenocarcinoma, Burkitt's Lymphoma, and viral infection suggesting possible links between miRNAs and viral disease, neurodevelopment, and cancer. There is speculation that in higher eukaryotes, the role of miRNAs in regulating gene expression could be as important as that of transcription factors.

Aberrant expression of miRNA, be it under- or overexpression, can result in many kinds of disorders. Recently many different miRNA were identified that relate to specific diseases. As many miRNAs, however, regulate several hundreds of genes, for most miRNA-related diseases it is hitherto unknown which gene is regulated by the identified miRNA and is ultimately responsible for the disease. For instance, Sayed et al. (Circ Res 2007; 100:416-424) have identified, amongst others, that several miRNAs show increased or decreased expression during cardiac hypertrophy. The most prominent up-regulated miRNA are miR-199a, miR-199a*, miR-199b, miR-21 and miR 214. Up to the present invention, however, it was not known which genes may be deregulated by the aberrant expression of these miRNAs and whether up-regulation or down-regulation of any of these miRNAs cause heart disease or are, for instance, only a result of heart disease.

The present invention provides for the first time the insight that increased expression of microRNA, for instance miR-199b, causes heart disease and that inhibiting microRNA inhibits cardiac hypertrophy. The present invention furthermore provides the insight that the dual-specificity tyrosine phosphorylation-regulated kinase 1A (Dyrk1a) is a direct target of miR-199b. It is, for instance, shown that an increase in expression of miR-199b causes a down-regulation of Dyrk1a and that this down-regulation of Dyrk1a causes, amongst other things, hypertrophy of myocardial cells, which leads eventually to heart failure. The Dyrk1a gene is localized on human chromosome 21 and, although its function is not completely understood, it has been associated with the (embryologic) development of the nervous system. Its over-expression has been associated with the learning and memory deficits of Down syndrome, development of Alzheimer's disease, and some other rare neurologic diseases (e.g., Pick's Disease). All diseases currently associated with Dyrk1a aberrant expression are of neurological origin. Up to the present invention, Dyrk1a has never been associated with heart disease, let alone heart failure. The present invention, however, provides the insight that an increase of Dyrk1a is able to prevent, diminish or delay heart muscle hypertrophy and thus heart failure. Increase of Dyrk1a expression can be achieved either directly or indirectly, for instance by inhibiting miR-199b.

Now that the invention has provided the insight that inhibition of Dyrk1a leads to cardiac hypertrophy and that increasing the expression, amount and/or activity of Dyrk1a and/or inhibition of a microRNA capable of inhibiting Dyrk1a is able to decrease cardiac hypertrophy, in a first embodiment, the invention provides a method for treating, diminishing, counteracting, delaying and/or preventing heart disease, comprising administering to an individual in need thereof a pharmaceutically effective amount of an inhibitor of a microRNA, wherein microRNA is capable of inhibiting or decreasing the expression of Dyrk1a. Hence, an inhibitor of a microRNA, microRNA being capable of inhibiting or decreasing the expression of Dyrk1a, is particularly suitable for use as a medicament. Further provided is, therefore, an inhibitor of microRNA for use in treating, diminishing, delaying and/or preventing heart disease, wherein microRNA is capable of inhibiting or decreasing the expression of Dyrk1a.

A use of such inhibitor for the preparation of a medicament is also provided. One embodiment thus provides a use of an inhibitor of microRNA, wherein microRNA is capable of inhibiting or decreasing the expression of Dyrk1a, for the manufacture of a medicament for treating, diminishing, delaying and/or preventing heart disease.

As used herein, the term "inhibitor of microRNA" comprises compounds that are capable of inhibiting or at least partly inhibiting the expression, the amount and/or the activity of microRNA. In case that expression of microRNA causes, aggravates and/or sustains a disease condition, inhibiting or partly inhibiting expression of microRNA will at least in part counteract, diminish, delay or prevent the disease condition. If expression of a microRNA in an individual is increased as compared to a normal, healthy situation, expression of microRNA is preferably restored to a normal value, preferably the expression level present in the individual before such increase took place.

Inhibition of microRNA is achieved through several methods. For instance, a nucleic acid molecule that is complementary to at least a functional part of microRNA is used. The functional part comprises at least 15 nucleotides, preferably at least 18 nucleotides, more preferably at least 20 nucleotides. After administration to a cell, the nucleic acid molecule then binds to microRNA, thereby counteracting, delaying and/or at least in part inhibiting binding of microRNA to the target gene and thereby counteracting the function of microRNA, i.e., gene regulation. A person skilled in the art is aware of various methods to inhibit or partly inhibit microRNA. Non-limiting examples are, for instance, the use of a locked nucleic acid oligo (LNA), in which an extra bridge connecting the 2' and 4' carbons is present, where the bridge "locks" the ribose in the 3'-endo structural conformation. Further, non-limiting examples comprise a Morpholino oligo, a modified antisense molecule that does not degrade its target RNA molecule, and a 2'-O-methyl RNA oligo.

Therefore, in a preferred embodiment, an inhibitor, a use and/or a method according to the invention are provided, wherein the inhibitor comprises a nucleic acid sequence with a length of at least 15 nucleotides, preferably at least 18 nucleotides, more preferably at least 20 nucleotides, that is complementary to microRNA.

There are several hundreds of distinct microRNA molecules and their precursors are clustered together based on their relative distance in the genome: In general, precursors are placed in the same cluster if they are 50 kb or less from each other away. As the invention provides the insight that Dyrk1a is a direct target of miR-199b, in a preferred embodiment, the invention provides an inhibitor of microRNA for use in treating, diminishing, delaying and/or preventing heart disease, wherein the inhibitor is capable of counteracting expression, amount and/or activity of microRNA miR-199b. An inhibitor, use and/or method according to the present invention, wherein the inhibitor is capable of counteracting expression, amount and/or activity of microRNA miR-199b, is, therefore, also provided.

An inhibitor of microRNA is especially useful if an efficient amount is able to reach a microRNA that it is supposed to inhibit. As microRNA is typically present inside a cell, the inhibitor is preferably able to inhibit microRNA inside the cell. As the inhibitor of microRNA is especially useful for the treatment or prevention of heart disease, the inhibitor is even more preferably able to inhibit expression, amount and/or activity of microRNA within a heart muscle cell. In one embodiment, the inhibitor is capable of being introduced into the cell, preferably a heart muscle cell. In one embodiment, the inhibitor of microRNA is itself able to penetrate a cell membrane and enter a cell, preferably a heart muscle cell. However, it is also possible to modify the inhibitor such, that it is thereafter capable of entering a cell, preferably a heart muscle cell. This is, however, not necessary because many transport systems capable of introducing a compound into a cell are known.

Thus, in a preferred embodiment, an inhibitor, a use and/or a method according to the invention is provided, wherein the inhibitor is capable of counteracting, inhibiting and/or decreasing the expression, amount and/or activity of microRNA in a cell, more preferably in a heart muscle cell.

A heart muscle cell, also called a cardiac muscle cell or a cardiomyocyte, is a cell similar to, originating from, or derived of a muscle cell, which in a natural situation, is present in the heart of a vertebrate organism. The cell need not to be directly obtained from heart tissue since it is also possible to culture and/or store this kind of cell in vitro.

Methods for introducing an inhibitor of microRNA into a cell are known in the art. Methods for introducing inhibitors, preferably antisense nucleic acid, comprise, for instance, calcium phosphate transfection, DEAE-Dextran, electroporation or liposome-mediated transfection. Alternatively, direct injection of the inhibitor is employed. Preferably however, a nucleic acid that is an inhibitor and/or that encodes an inhibitor is introduced into a cell by a vector, preferably a viral vector. Various terms are known in the art that refer to introduction of nucleic acid into a cell by a vector. Examples of such terms are "transduction," "transfection" and "transformation." Techniques for generating a vector with a nucleic acid sequence and for introducing the vector into a cell are known in the art. Marker genes such as, for instance, antibiotic resistance or sensitivity genes and/or genes encoding markers such as cell surface antigens or fluorescent proteins like green fluorescence protein are preferably used in identifying cells containing the introduced nucleic acid, as is well known in the art.

Preferably, an inhibitor according to the invention is provided that is able to be introduced into a mammalian cell in vivo. Non-limiting examples of methods according to the invention are the coupling of the inhibitor to cell-penetrating peptides, or the use of liposomes containing the inhibitor. Preferably, the inhibitor is targeted to heart muscle cells, for instance by using artificial HDL-like particles bound to the inhibitor, enhancing delivery to the myocardium.

Inhibition of microRNA in a cell, wherein microRNA is capable of inhibiting or decreasing the expression of Dyrk1a, leads to an increase or restoration of Dyrk1a expression in the cell. In a preferred embodiment, therefore, an inhibitor, use and/or method according to the invention is provided wherein the inhibitor of microRNA is capable of increasing and/or restoring the expression of Dyrk1a in a cell. To be able to counteract the function of microRNA in a cell, the inhibitor is preferably able to penetrate the nucleus. It is generally accepted that small nucleic acid molecules, preferably antisense molecules, such as the before mentioned LNA, Morpholino, or 2'-O-methyl RNA oligos, can freely move between the cytosol and the nucleus. In one embodiment, however, an inhibitor that is not able to freely move between the cytosol and the nucleus is modified such as to target and penetrate the nuclear membrane. Methods to target the nucleus are well known in the art and include, for instance, the use of nuclear targeting vector, such as an adenovirus vector.

In a preferred embodiment, an inhibitor of microRNA, a use and/or a method according to the invention is provided, wherein the inhibitor comprises an antisense nucleic acid molecule. Preferably, an antisense nucleic acid molecule against a microRNA capable of inhibiting or decreasing the expression of Dyrk1a is used. The antisense molecule preferably comprises at least 15 nucleotides. Even more preferably, the antisense molecule comprises at least 18 nucleotides. Most preferably, the antisense molecule comprises at least 20 nucleotides.

As said before, the invention provides the insight that miR-199b decreases the expression of Dyrk1a, which is involved with, and/or enhances, heart disease. Therefore, an inhibitor of the invention preferably inhibits miR-199b. An inhibitor, use and/or method according to the invention wherein microRNA is miR-199b is, therefore, also provided. Preferably, the inhibitor of miR-199b comprises a nucleic acid sequence able to bind to miR-199b under physiological conditions. FIG. 6, Panel a, comprises a non-limiting example of a sequence that is capable of binding to miR-199b. It is commonly thought that to be able to bind and inhibit the function of microRNA, an antisense nucleic acid is allowed to have a few (preferably 1 or 2) mismatches. Thus, for instance in the case of a sequence as depicted in FIG. 6, Panel a, at least 20 nucleotides are preferably identical to the complementary sequence of miR-199b. Moreover, an antisense nucleic acid is allowed to be somewhat shorter than its target sequence. An antisense against miR-199b is preferably at least 20 nucleotides long. In a preferred embodiment, therefore, an inhibitor, use and/or method according to the invention is provided, wherein the inhibitor comprises a nucleic acid molecule comprising a sequence with a length of at least 18, preferably at least 20 nucleotides with at least 90% sequence identity to at least 18, preferably at least 20 nucleotides of miR-199b, or the complement thereof. In one embodiment, the nucleic acid molecule comprises a sequence with a length of at least 20 nucleotides with at least 90% sequence identity to at least part of a sequence shown in FIG. 6, Panel a, the part having at least 20 nucleotides. The nucleic acid sequence is preferably at least 90% identical to the sequence GAACAGGUAGUC-UAAACACU (SEQ ID NO:1).

One particularly preferred embodiment provides an inhibitor, a use, and/or a method according to the invention, wherein the inhibitor comprises:
  a nucleic acid sequence with a length of at least 20 nucleotides with at least 90% sequence identity to at least part of the sequence CCCAGUGUUUAGACUAUCUG-UUC (hsa-miR-199b-5p) (SEQ ID NO:2) or the complement thereof, the part having at least 20 nucleotides, and/or
  a nucleic acid sequence with a length of at least 20 nucleotides with at least 90% sequence identity to at least part of the sequence ACAGUAGUCUGCACAUUGGUUA (hsa-miR-199b-3p) (SEQ ID NO:3) or the complement thereof, the part having at least 20 nucleotides. Such nucleic acid sequence with a length of at least 20 nucleotides is particularly suitable for counteracting miR-199b, thereby increasing and/or restoring Dyrk1a expression in a cell. Hence, as a result, such nucleic acid sequence is particularly suitable for counteracting heart disease and for the preparation of a medicament for counteracting and/or preventing heart disease.

The term "% sequence identity" is defined herein as the percentage of nucleotides in a nucleic acid sequence that is identical with the nucleotides in a nucleic aid sequence of interest, after aligning the sequences and optionally introducing gaps, if necessary, to achieve the maximum percent sequence identity. Methods and computer programs for alignments are well known in the art. As used herein, the terms "nucleic acid sequence" and "nucleotides" also encompass non-natural molecules based on and/or derived from nucleic acid sequences such as, for instance, artificially modified nucleic acid sequences, peptide nucleic acids, as well as nucleic acid sequences comprising at least one modified nucleotide and/or non-natural nucleotide such as, for instance, inosine.

An inhibitor as described above is thus especially suitable for the manufacture of a medicament for treating, diminishing, delaying and/or preventing heart disease, preferably heart failure. In one embodiment, the invention, therefore, provides a use of an inhibitor of microRNA, wherein microRNA is capable of inhibiting or decreasing the expression of Dyrk1a, for the manufacture of a medicament for treating, diminishing, delaying and/or preventing heart disease, preferably heart failure. In a preferred embodiment, a use according to the invention is provided, wherein the inhibitor comprises a nucleic acid molecule that is complementary to at least 15 nucleotides, preferably at least 18 nucleotides, most preferably at least 20 nucleotides of microRNA. Further provided is a use according to the invention, wherein the inhibitor is capable of counteracting expression, amount and/or activity of microRNA miR-199b. In a preferred embodiment, the inhibitor is capable of inhibiting or decreasing the expression of microRNA in a cell, preferably thereby increasing or restoring the expression of Dyrk1a in the cell. The cell preferably is a heart muscle cell. In yet another preferred embodiment, a use according to the invention is provided, wherein the inhibitor comprises an antisense nucleic acid molecule with a length of at least 20 nucleotides, preferably with at least 90% sequence identity to a sequence shown in FIG. 6, Panel a, or the complement thereof. Particularly preferred antisense nucleic acid sequences are sequences with a length of at least 20 nucleotides with at least 90% sequence identity to at least part of the sequence CCCAGUGUUUA-GACUAUCUGUUC (hsa-miR-199b-5p) (SEQ ID NO:2) or ACAGUAGUCUGCACAUUGGUUA (hsa-miR-199b-3p) (SEQ ID NO:3), or the complement of any of these sequences, the part having at least 20 nucleotides. In one preferred embodiment, the invention, therefore, provides a use of a nucleic acid sequence with a length of at least 20 nucleotides with at least 90% sequence identity to at least part of the sequence CCCAGUGUUUAGACUAUCUGUUC (hsa-miR-199b-5p) (SEQ ID NO:2) or the complement thereof, the part having at least 20 nucleotides, for the manufacture of a medicament for treating, diminishing, delaying and/or preventing heart disease, preferably heart failure. Another preferred embodiment provides a use of a nucleic acid sequence with a length of at least 20 nucleotides with at least 90% sequence identity to at least a part of the sequence ACAGUAGUCUGCACAUUGGUUA (hsa-miR-199b-3p) (SEQ ID NO:3) or the complement thereof, the part having at least 20 nucleotides, for the manufacture of a medicament for treating, diminishing, delaying and/or preventing heart disease, preferably heart failure.

With a use according to the invention it is thus possible to treat, diminish, delay or at least partly prevent a heart disease.

In one embodiment, the invention provides a method for treating, diminishing, counteracting, delaying and/or preventing a heart disease, comprising administering to an individual in need thereof a pharmaceutically effective amount of an inhibitor of microRNA, wherein microRNA is capable of inhibiting or decreasing the expression of Dyrk1a. In one embodiment, the individual is diagnosed with a heart disease before treatment. A method comprising determining whether a subject is suffering from heart disease and, if the subject appears to be suffering from heart disease, treating the person with a method according to the present invention, is, therefore, also provided.

Preferably, a method according to the invention is provided, wherein the inhibitor comprises a nucleic acid sequence with a length of at least 15, preferably at least 18, most preferably at least 20 nucleotides that is at least 90% complementary to microRNA, which nucleic acid sequence is preferably capable of counteracting expression, amount and/or activity of microRNA miR-199b. The nucleic acid sequence is preferably at least 90% complementary to miR-199b. Even more preferred, a method according to the invention is provided in which the inhibitor is capable of inhibiting or decreasing the expression of microRNA in a cell, even more preferably in a heart muscle cell. In yet another preferred embodiment, a method according to the invention is provided, wherein the inhibitor comprises an antisense nucleic acid molecule, preferably with a length of at least 20 nucleotides with at least 90% sequence identity to a sequence shown in FIG. 6, Panel a, or the complement thereof.

In another embodiment of the invention, a method for counteracting expression of microRNA is provided, wherein an inhibitor according to the invention is expressed in a target cell. In one embodiment, a vector is used that comprises a nucleic acid sequence comprising and/or encoding the inhibitor according to the invention.

The invention thus also provides a vector comprising a nucleic acid sequence, which sequence comprises or encodes an inhibitor of microRNA expression, wherein microRNA is capable of inhibiting or decreasing the expression of Dyrk1a. The vector preferably comprises a retroviral, adenoviral, adeno-associated viral, or lentiviral vector.

As already described above, it is preferred to increase the expression, amount and/or activity of Dyrk1a in order to counteract, delay or at least partly prevent heart disease. This can be achieved either indirect, for instance by decreasing the expression, amount and/or activity of miR-199b, or direct, through increasing the expression, amount and/or activity of Dyrk1a. Expression, amount and/or activity of miR-199b are preferably counteracted by a nucleic acid sequence that is at least 90% complementary to at least 18, preferably at least 20 nucleotides of miR-199b. Further provided is, therefore, a vector according to the invention, comprising a nucleic acid molecule with a length of at least 18 nucleotides that is at least 90% complementary to at least 18 nucleotides of microRNA miR-199b. The vector preferably comprises:

- a nucleic acid sequence with a length of at least 20 nucleotides with at least 90% sequence identity to at least a part of the sequence CCCAGUGUUUAGACUAUCU-GUUC (hsa-miR-199b-5p) (SEQ ID NO:2) or the complement thereof, the part having at least 20 nucleotides, and/or
- a nucleic acid sequence with at least 90% sequence identity to at least a part of the sequence ACAGUAGUCUGCA-CAUUGGUUA (hsa-miR-199b-3p) (SEQ ID NO:3) or the complement thereof, the part having at least 20 nucleotides.

As said before, it is also possible to increase the expression, amount and/or activity of Dyrk1a directly. This can, for instance, be achieved through the use of a vector comprising or encoding a Dyrk1a increasing compound.

One embodiment provides a vector according to the invention comprising a promoter suitable for expression in a mammalian cell. In one embodiment, the promoter is operably linked to a nucleic acid molecule capable of increasing the expression, amount and/or activity of Dyrk1a. In another embodiment, the promoter is operably linked to a nucleic acid molecule capable of counteracting expression, amount and/or activity of miR-199b microRNA. In a particularly preferred embodiment, a vector according to the invention is suitable for expression in a heart muscle cell. In that case, the vector preferably comprises a promoter suitable for expression in a heart muscle cell. In one embodiment, a vector according to the invention comprises a ubiquitous promoter or an organ-specific promoter, preferably a heart muscle cell-specific promoter. Such a vector is especially useful for treating, diminishing, delaying and/or preventing heart disease. In one embodiment, therefore, the invention provides a use of a vector according to the invention for the preparation of a medicament for treating, diminishing, delaying and/or preventing heart disease.

The invention also provides an isolated cell comprising a vector and/or an inhibitor according to the invention. The cell preferably comprises a mammalian cell. In one particularly preferred embodiment, the cell comprises a heart muscle cell. Such an isolated cell comprising a vector and/or an inhibitor according to the invention is especially useful for treating, diminishing, delaying and/or at least in part preventing heart disease. In one embodiment, therefore, an isolated cell comprising a vector and/or an inhibitor according to the invention for the use in treating, diminishing, delaying and/or preventing heart disease is provided.

Preferably, the isolated cell comprises a heart muscle cell, a heart muscle progenitor cell or a stem cell. In one embodiment, such heart muscle, progenitor or stem cell is injected into a heart muscle, preferably into a damaged part of a heart, where the cell is capable of expanding and repairing the damaged part. In another embodiment, a cell according to the invention is injected into the circulation of an individual, allowing the cell to engraft into the heart of the individual, preferably into a damaged part of the heart, and (at least partly) repair the damaged part.

In a preferred embodiment, an isolated cell according to the invention is provided, wherein a nucleic acid sequence comprising or encoding an inhibitor according to the invention is present. The nucleic acid sequence is preferably operably linked to an exogenous regulatory element that is specific for myocardial cells. The exogenous regulatory element is, for instance, operably linked to an antisense nucleic acid of miR-199b, which antisense nucleic acid is at least 90% identical to at least 18 nucleotides, preferably at least 20 nucleotides of miR-199b, in order to enhance expression of the antisense nucleic acid in myocardial cells. A use of an exogenous regulatory element that is specific for myocardial cells provides various advantages. For instance, after transduction of stem cells and/or progenitor cells, an inhibitor according to the invention will not be expressed in all kinds of differentiated cells, but mainly in myocardial cells, facilitating enrichment and/or isolation of myocardial cells.

An isolated cell according to the invention comprising a vector and/or an inhibitor is also especially useful for the preparation of a medicament, preferably for treating, diminishing, delaying and/or preventing heart disease. The invention thus also provides a use of an isolated cell comprising a vector and/or an inhibitor according to the invention for the preparation of a medicament, preferably for treating, diminishing, delaying and/or preventing heart disease.

Furthermore a method is provided for treating, diminishing, delaying and/or preventing a heart disease, comprising administering to an individual in need thereof a pharmaceutically effective amount of a vector and/or a cell according to the invention. The invention further provides a pharmaceutical composition comprising an inhibitor of microRNA, wherein microRNA is capable of inhibiting or decreasing the expression of Dyrk1a, the pharmaceutical composition further comprising a pharmaceutically acceptable carrier, diluent or excipient. The inhibitor preferably comprises a miR-199b inhibitor, preferably a nucleic acid sequence with a length of at least 18, preferably at least 20 nucleotides, which is at least 90% identical to at least 18, preferably at least 20 nucleotides of miR-199b or the complement thereof. A pharmaceutical composition comprising a vector and/or an isolated cell according to the invention, further comprising a pharmaceutically acceptable carrier, diluent or excipient, is also provided. Suitable carriers, diluents, excipients and the like are commonly known in the art of pharmaceutical formulation and may be readily found and applied by the skilled artisan in references such as, for instance, Remington's Pharmaceutical Sciences, Mace Publishing Company, Philadelphia Pa., 17th ed. 1985.

A pharmaceutical composition according to the invention is presented in any form, for example as a tablet, as an injectable fluid or as an infusion fluid etc. Moreover, the inhibitor, vector and/or cell according to the invention can be administered via different routes, for example intravenously, bronchially, or orally. Yet another suitable route of administration is local injection, preferably into the heart muscle.

In a preferred embodiment, the used route of administration is intravenously. It is clear for the skilled person that preferably a therapeutically effective amount of an inhibitor, vector and/or cell according to the invention is delivered. Dose ranges of inhibitors, vectors, cells and/or other molecules according to the invention to be used in the therapeutic applications as described herein are designed on the basis of rising dose studies in the clinic in clinical trials for which rigorous protocol requirements exist. As a starting point, a dose of between 0.01 and 100 mg/kg/day is used.

The present invention provides the insight that inhibition of Dyrk1a leads to heart disease that can be counteracted, diminished, delayed and/or prevented by increasing the expression, amount and/or activity of Dyrk1a and/or inhibition of a microRNA capable of inhibiting Dyrk1a. The invention, therefore, further provides a use, a method, a vector, an inhibitor, an isolated cell, and/or a pharmaceutical composition according to the invention, wherein the heart disease is associated with microRNA expression and/or decreased or inhibited expression of Dyrk1a. Preferably, the microRNA is miR-199b.

Decreasing the expression, amount and/or activity of miR-199b and/or increasing the expression, amount and/or activity of Dyrk1a is particularly useful for counteracting, diminishing, delaying or at least in part preventing hypertrophic heart disease and/or heart failure and/or a heart disease that is related to a condition after heart-ischemia, diabetes, hypertension, and/or at least one inherited genetic mutation that causes any form of early- or late-onset congenital heart disease.

Further provided is, therefore, a use, a method, a vector, an inhibitor, an isolated cell, and/or a pharmaceutical composition according to the invention, wherein the heart disease is hypertrophic heart disease, preferably heart failure. In a preferred embodiment, the heart disease is associated with a condition after heart-ischemia, diabetes, and/or hypertension, and/or related associated with at least one inherited genetic mutation that causes early- or late-onset congenital heart disease. In a preferred embodiment, the invention provides a method for counteracting, diminishing, treating, delaying or preventing a heart disease associated with a condition after heart-ischemia, diabetes, and/or hypertension, and/or associated with at least one inherited genetic mutation that causes a form of early or late-onset congenital heart disease, comprising administering to a subject in need thereof a pharmaceutically effective amount of a vector, an inhibitor, an isolated cell, and/or a pharmaceutical composition according to the invention, preferably after the subject has been diagnosed with the heart disease.

In yet another embodiment, the invention provides a non-human test animal that has been provided with an inhibitor of microRNA, wherein microRNA is capable of inhibiting or decreasing the expression of Dyrk1a. The inhibitor preferably comprises a miR-199b inhibitor. A non-human test animal that has been provided with a vector, an isolated cell, and/or a pharmaceutical composition according to the invention is also provided. Such a non-human test animal is especially useful for screening, detection and/or identification of candidate compounds capable of inhibiting or decreasing expression, amount and/or activity of miR-199b. Such non-human test animal is also especially useful for screening, detection and/or identification of candidate compounds capable of increasing and/or restoring the expression, amount and/or activity of Dyrk1a. Hence, a non-human test animal according to the invention is especially useful for screening, detection and/or identification of candidate compounds capable of counteracting, diminishing, delaying or preventing heart disease.

Screening methods for candidate compounds are especially useful for identifying new inhibitors and are, therefore, also herewith provided. A screening method, for instance, comprises contacting a candidate compound with an isolated cell and measuring the expression, amount and/or activity of miR-199b and/or Dyrk1a. The expression, amount and/or activity of miR-199b and/or Dyrk1a is preferably compared with the expression, amount and/or activity of miR-199b and/or Dyrk1a in the same kind of cell or animal without the candidate compound. A decreased miR-199b and/or increased Dyrk1a expression, amount and/or activity relative to the cell or animal without the candidate compound indicates that the candidate compound is able to counteract and/or prevent heart disease.

Further provided is thus a method for determining whether a candidate compound is able to counteract and/or prevent heart disease, comprising contacting the candidate compound with an isolated cell and/or a non-human test animal and measuring expression, amount and/or activity of miR-199b and/or Dyrk1a in the cell and/or the animal, further comprising comparing the measured expression, amount and or activity with the expression, amount and or activity of miR-199b and/or Dyrk1a in the same kind of cell or animal without the candidate compound, wherein decreased miR-199b and/or increased Dyrk1a expression, amount and/or activity relative to the cell or animal without the candidate compound indicates that the candidate compound is able to counteract and/or prevent heart disease. Preferably, the candidate compound is contacted with a cell that shows increased miR-199b and/or decreased Dyrk1a expression, amount and/or activity as compared to a healthy cell or animal. The increase in miR-199b and/or decrease in Dyrk1a expression, amount and/or activity preferably results in hypertrophy in the cell. Contacting the hypertrophic cell with a candidate compound and measuring the expression, amount and/or activity of miR-199b and/or Dyrk1a and/or measuring the shape and size of the cell, and comparing the measurements with reference values, for instance, of the cell before contacting the cell with the candidate compound or, for instance, an isolated cell that is not contacted with the candidate compound, identifies compounds that are able to inhibit miR-199b, increase Dyrk1a expression, amount and/or activity, and/or decrease or inhibit hypertrophy of the cell.

One embodiment provides a screening method comprising administering a candidate compound to a non-human test animal and measuring the expression, amount and/or activity of miR-199b and/or Dyrk1a and comparing the measurement(s) with a reference value as described above. Preferably, the non-human test animal exhibits increased miR-199b and/or decreased Dyrk1a expression, amount and/or activity before contacting the cell or the animal with the compound. The invention provides the insight that such a non-human test animal is at higher risk of developing heart disease, in particular heart failure. Contacting the animal with an inhibitor according to the invention will counteract, prevent, delay or diminish the heart disease. Such an animal is thus especially useful for screening a candidate compound for its ability of preventing, treating, delaying and/or diminishing heart disease. Additionally, or alternatively, a cell according to the invention is used. In one embodiment, therefore, the invention provides a method for screening a candidate compound, comprising contacting the candidate compound with an isolated cell and/or a non-human test animal and measuring expression, amount and/or activity of miR-199b and/or Dyrk1a in the cell and/or the animal and comparing the measurement with a reference value obtained, for instance, from the cell or the animal before contacting the cell or the animal with the candidate compound or, for instance, from another cell or animal that is not contacted with the candidate compound. A decrease in miR-199b and/or increase in Dyrk1a expression, amount and/or activity demonstrates that the candidate compound is able to counteract and/or prevent heart disease, in particular heart failure.

In a preferred embodiment, the candidate compound is contacted with an isolated cell or non-human test animal exhibiting increased miR-199b or decreased Dyrk1a expression, amount and/or activity as compared to a normal, healthy cell or animal of the same kind. An isolated cell exhibiting increased miR-199b and/or decreased Dyrk1a expression, amount and/or activity, is especially useful because it changes its shape and size, i.e., the cell becomes hypertrophic. Counteracting the increase of miR-199b and/or decrease of Dyrk1a counteracts the change in shape and size and such a cell is thus particularly useful for screening purposes, as the read-out of the screening is easily performed, for instance with a microscope. A non-human test animal exhibiting increased miR-199b and/or decreased Dyrk1a expression, amount and/or activity is also particularly useful for screening purposes, because such an animal is developing heart disease or is at risk of developing heart disease. A candidate compound capable of counteracting and/or preventing heart disease is thus easily identified in the animal.

The invention thus provides a screening method comprising contacting a candidate compound with an isolated cell or non-human test animal, preferably showing increased miR-199b or decreased Dyrk1a expression, amount and/or activity, further comprising assessing the shape and/or size of the isolated cell and/or the severity and/or risk of heart disease, preferably heart failure, in the non-human test animal and comparing the size and/or shape of the cell, and/or severity and/or risk of the heart disease in the non-human test animal a reference value. The reference value may be obtained from the same cell or same animal, for instance before contacting the cell or animal with the candidate compound. The reference value may also be obtained from another cell or animal, which, for instance, is not contacted with the candidate compound. A change in value, preferably a decrease in cell size and/or a decrease in risk and/or severity of heart disease indicates whether the candidate compound is able to counteract heart disease.

One preferred embodiment, therefore, provides a method for determining whether a candidate compound is able to counteract and/or prevent heart disease, comprising contacting the candidate compound with an isolated cell and/or a non-human test animal, wherein the isolated cell and/or the non-human test animal preferably shows increased miR-199b or decreased Dyrk1a expression, amount and/or activity, and wherein the shape and size of the isolated cell and/or the severity and/or risk of developing a heart disease, preferably heart failure in the non-human test animal is measured, further comprising comparing the measured expression, amount and/or activity, the shape and/or size, and/or the risk and/or severity with the corresponding values of the same kind of cell or non human animal without the candidate compound, wherein decreased miR-199b and/or increased Dyrk1a expression, amount and/or activity, a change in size and shape, preferably a decrease in size, and/or a decrease in risk and/or severity of heart disease, relative to the cell or non human animal without the candidate compound, indicates that the candidate compound is able to counteract and/or prevent heart disease.

Candidate compounds, identified with a method according to the present invention, are especially useful for the treatment of miR-199b related and/or Dyrk1a related diseases, for instance through inhibition of miR-199b, including the treatment of heart disease, preferably heart failure. Such compounds, as well as their use against heart disease as well as their use for the preparation of a medicament against heart disease, are, therefore, also provided.

The invention provides the insight that heart disease, for instance heart failure, is related to decreased expression of Dyrk1a and that miR-199b is able to accomplish just this. However, as outlined before, there are hundreds of microRNAs already known, and a number of several thousand different microRNAs has been predicted to exist in mammalians, and each and every one of them is generally thought to regulate hundreds of genes. Thus, next to miR-199b, there are other microRNAs that are capable of regulating expression of Dyrk1a. Any of these microRNAs are useful for increasing or restoring the expression of Dyrk1a. It is also possible to indirectly inhibit or decrease the expression of miR-199b, e.g., through manipulation of transcription factors that regulate miR-199b, thereby indirectly increasing the expression of Dyrk1a. The current views in the art suggest that miRNA expression is mainly controlled at the transcriptional level.

In one embodiment, therefore, the invention further provides a method for treating, diminishing, delaying or preventing a heart disease, comprising decreasing or inhibiting expression of miR-199b and/or increasing or restoring the expression, amount and/or activity of Dyrk1a in a subject suffering from, or at risk of suffering from, the heart disease.

It is of course also possible to directly influence Dyrk1a without the use of for instance miR-199b. It is, for instance, possible to increase expression, amount and/or activity of endogenous Dyrk1a or to administer exogenous Dyrk1a and/or a nucleic acid encoding Dyrk1a in order to increase the amount and/or (overall) activity of Dyrk1a.

In yet another embodiment, the invention thus provides a compound capable of increasing or restoring the expression, amount and/or activity of Dyrk1a for use as a medicament. A compound capable of increasing or restoring the expression, amount and/or activity of Dyrk1a is preferably used in treating, diminishing, delaying and/or preventing heart disease, or for the preparation of a medicament against heart disease. In one preferred embodiment, the compound comprises a nucleic acid sequence comprising a sequence encoding Dyrk1a or a functional equivalent thereof.

The invention is further explained in the following examples. These examples do not limit the scope of the invention, but merely serve to clarify the invention.

DETAILED DESCRIPTION OF THE INVENTION

Examples

Materials and Methods

Figure 1:
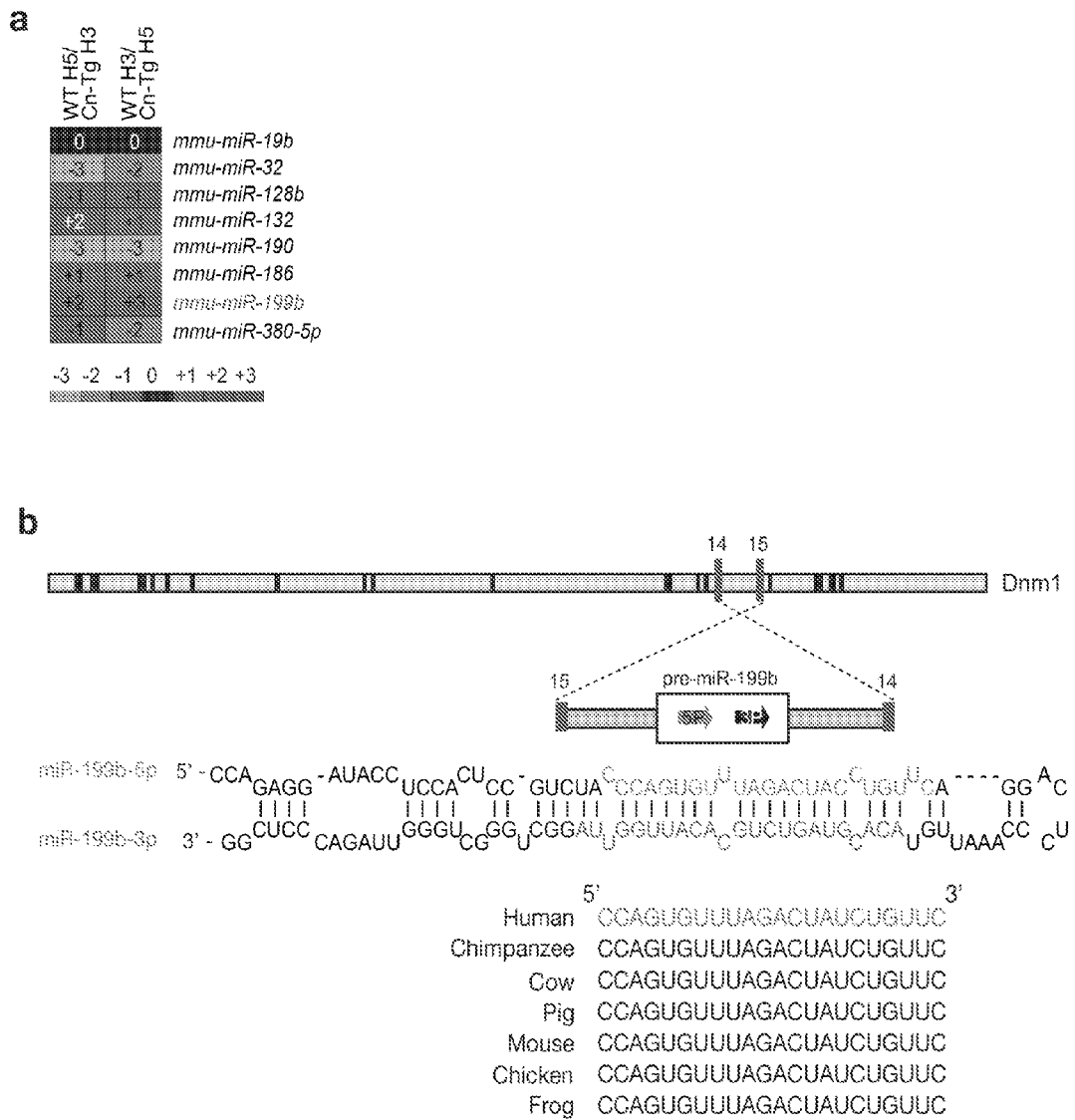
FIG. 1: Genomic localization of MicroRNA-199b. Panel a: MicroRNA profiling reveals a set of microRNAs that were differentially expressed in cardiac tissue from two-month-old alphaMHC-CnA (αMHC-CnA) transgenic mice. Panel b: Genomic localization of the intragenic microRNA miR-199b, located on chromosome 9, on the opposite strand in the Dnm1 gene. (Cf. SEQ ID NOS:4 (miR-199b-5p) and 14 (miR-199b-3p).)

Mice.

As experimental animal models we made use of two-month-old wild-type B6CBA and MHC-CnA transgenic mice, which express an activated mutant of calcineurin under control of the 5.5 kb murine cardiac a-myosin heavy chain (Myh6) promoter.[1,2] All protocols were performed according to institutional guidelines and were approved by local Animal Care and Use Committees.

Aortic Banding.

Transverse aortic banding (TAC) or sham surgery was performed in two-month-old wild-type B6CBA by subjecting the aorta to a defined, 27 gauge constriction between the first and second truncus of the aortic arch as described previously in detail.[3] Doppler echocardiography was used to calculate the pressure gradient between the proximal and distal sites of the transverse aortic constriction using the Doppler-estimated Bernoulli's equation,[4] and only mice with a pressure gradient >20 mm Hg were included.

RNA Isolation from Mouse Tissue or Stable Mammalian Cell Lines.

We isolated total RNA from different mouse tissues or from cultured mammalian cells. Wild-type and MHC-CnA transgenic mice were sacrificed by cervical dislocation under isofluorane anesthesia. Whole hearts and small samples of brain, thymus, kidney, intestine, colon and testis were removed, cleaned in PBS, placed in a labeled tube containing 1 ml of TRIzol reagent (Invitrogen) and immediately put into liquid nitrogen. Tissues were homogenized several times at maximum speed, each time for about one minute (to prevent overheating), until complete disruption. Cells cultured in six-well plates to 100% of confluency were washed twice with PBS before adding 1 ml of Trizol per well and collecting the cell lysates in RNase-free tubes. After shaking the homogenates for ten minutes at 4° C. (to permit the complete dissociation of nucleoprotein complexes), 0.3 ml of chloroform per 1 ml of TRIzol were added to each sample. Centrifugation at 12,000 g for 15 minutes at 4° C. results in the separation of RNA (upper aqueous phase) from DNA and proteins (organic lower and intermediate phase). Aqueous phases (60% of the sample volume) were collected in new RNase-free tubes and RNA was precipitated with 0.5 ml of isopropanol by incubation at −20° C. for at least one hour and centrifugation at 12,000 g for 30 minutes at 4° C. The pellets, containing the RNA, were washed twice with 1 ml of 70% ethanol at 12,000 g for five minutes at 4° C. After decantation of the ethanol and total removal by evaporation, samples were dissolved in 20-30 µl of RNase-free water. RNA quantity from the individual tissues was measured with a NanoDrop® ND-1000 UV-Vis Spectrophotometer (Wilmington), and RNA quality was monitored using an Agilent 2100 bioanalyzer.

Exiqon MicroRNA Expression Profiling and Data Analysis.

The expression analysis of 483 miRNA was performed by a miRNA-profiling service (Exiqon, Denmark) using miR-CURY LNA arrays. In short, two µg of total RNA pooled from three samples (three MHC-CnA transgenic hearts) and reference pool (three nontransgenic hearts) were labeled with Hy3™ and Hy5™ fluorescent label, respectively, using the miRCURY™ LNA Array labeling kit. The Hy3™-labeled samples and a Hy5™-labeled reference pool RNA sample were mixed pair-wise and hybridized to the miRCURY™ LNA array version 8.1, which contains capture probes targeting all miRNAs for all species registered in the miRBASE version 8.1 at the Sanger Institute. The hybridization was performed according to the miRCURY™ LNA array manual using a Tecan HS4800 hybridization station (Tecan, Austria). After hybridization, the microarray slides were scanned and stored in an ozone free environment (ozone level below 2.0 ppb) in order to prevent potential bleaching of the fluorescent dyes. The LNA array slides were scanned using the Agilent G2505B Microarray Scanner System (Agilent Technologies, Inc., USA) and image analysis was carried out using the ImaGene 7.0 software (BioDiscovery, Inc., USA). The raw signal for each probe was obtained by subtracting the maximum of the local background and negative control signals from the foreground signal. The data was pre-processed to remove poor-quality spots and normalization was used to remove any systematic bias. Quantified signals were normalized using the global Lowess (LOcally WEighted Scatterplot Smoothing) regression algorithm (Exiqon).

Northern Blotting.

Three micrograms of total RNA from heart or other different tissues were fractionated on a denaturing 12% polyacrylamide gel containing 8 M urea, transferred to Nytran N membrane (Schleicher & Schuell, Germany) by capillary method and fixed by UV cross-linking according to the manufacturer's instructions. Membranes were hybridized with specific 5'-Digoxigenin (Dig)-labeled LNA detection probes (Exiqon) for miR-199b or U6 (loading control). Detection was performed with an antibody against Dig (Roche).

Recombinant Adenoviruses, LNA Oligonucleotides and miRNA Precursor Molecules.

An adenovirus expressing an activated mutant of calcineurin (AdCnA) was described earlier.[5] AdLacZ was described previously.[6] Antisense oligonucleotides targeting miR-199b were obtained from Exiqon (miRCURY LNA knockdown oligo mmu-miR-199b, LNA-miR-199b) and miR-199b precursor molecules were obtained from Ambion (Pre-miR™ mmu-miR-199b miRNA Precursor, pre-miR-199b).

Primary Neonatal Rat Cardiomyocyte Cultures.

Neonatal rat ventricular myocytes were obtained by enzymatic dissociation of one- to two-day-old rat neonatal ventricles as described previously in detail.[7] Ventricles were stored in HEPES buffered DMEM (pH 7.4) prior to multiple rounds of enzymatic digestion in DMEM nutrient mixture F-12 Ham base (Sigma) supplemented with 0.7 mg/ml collagenase type 2 (Invitrogen) and 1 mg/ml pancreatin (Sigma). Cells were collected by centrifugation at 61×g for ten minutes, resuspended in neonatal calf serum (Invitrogen) and stored in an incubator at 37° C. All cell suspensions were pooled, centrifuged at 61×g for ten minutes and resuspended in DMEM (Invitrogen) supplemented with 10% horse serum (Invitrogen) and 5% fetal calf serum (Invitrogen). Subsequently, the cells were differentially plated for three hours in uncoated cell culture dishes to remove contaminating non-myocytes. The cardiomyocytes (containing less than 5% non-myocytes) were then plated on fibronectin (Sigma)-coated six-well culture dishes. Approximately 24 hours after plating the media was replaced by DMEM:M199 (4:1) medium (serum free medium).

Transient Transfection of Primary Neonatal Cardiomyocytes.

For transfection, neonatal rat cardiomyocytes were plated in DMEM supplemented with Nutridoma (Roche) in six-well fibronectin-coated plates with density of $2*10^5$ cells per well. The next day, cells were transiently transfected with 30 nM of LNA-miR-199b, pre-miR-199b or respective scrambled controls, with oligofectamine reagent (Invitrogen) according to the manufacturer's recommendations. Cells were washed the next day and left untreated, stimulated with 10 µM phenylephrine (PE), or infected with AdLacZ or AdCnA for 24 hours before cell fixation or RNA isolation.

Immunocytochemistry and Confocal Microscopy.

To visualize cardiomyocyte size and sarcomeric organization, cultured cardiomyocytes were fixed for ten minutes in 4% paraformaldehyde and permeabilized with 0.2% Triton X-100 in PBS for five minutes. Primary and secondary antibodies were diluted using 1% BSA in TBS and incubations were carried out at room temperature for one hour. Cells were washed three times with PBS for five minutes, mounted with coverslips in Vectashield mounting medium for fluorescence (Vector Laboratories), and analyzed by confocal microscopy using a Zeiss LSM 510 META microscope. Antibodies used included mouse monoclonal anti α-actinin (Sigma, 1:500); rabbit polyclonal anti ANF (Peninsula Laboratories) Cy5 goat anti-rabbit and Cy3 goat anti-mouse (Jackson Immuno Research, 1:100 and 1:500, respectively); and TOPRO-3 (1:100, Invitrogen). Cell surface areas were determined using SPOT-imaging software (Diagnostic Instruments) on 80-100 cardiomyocytes in 10 to 20 fields in three independent experiments.

Target Prediction, Primer Designing and Real-Time PCR.

To find the target genes of a specific microRNA we made use of several web servers based on predictive bioinformatics algorithms (PicTar, miRanda, miRBase). These are intuitive interfaces that incorporate processing algorithms and powerful miRNA targets search tools to search the miRNA targets against the most conserved 3' UTR sequences from UCSC Genome Browser. By comparing the target gene lists resulting from each algorithm we shortened the initial lists of hundreds of potential target genes to a list of 32 genes, common to all algorithms used.

We designed primers targeted against transcripts of 20 of the predicted genes and L7. The primers were specific for mouse sequences (www.ensembl.org) and selected using Beacon Designer software (Invitrogen) based on the following requirements: i) primer melting temperature of ~60° C., ii) GC-content of ~55%, iii) preferably no G at 5' end, iv) avoid runs of more than three identical nucleotides, and v) amplicon length of ~100 nucleotides. Specificity was checked with the Basic Local Alignment Search Tool (BLAST) and the specific melting point of the amplicons was analyzed using Biorad Dissociation curve software (iCycler, Biorad). All primer sets were tested for PCR efficiency and alternative primers were designed in case they fell outside the 5% efficiency range ($3.14 \leq slope \leq 3.47$). Three µg of RNA from indicated hearts was reverse-transcribed using Superscript II reverse transcriptase (Invitrogen). PCR amplification was performed (in duplicate) as a singleplex reaction with 400 nM forward and reverse primers on 40 ng cDNA, in a total reaction volume of 25 µl. The PCR was cycled between 95° C./30 seconds and 60° C./30 seconds for 40 cycles, following an initial denaturation step at 95° C. for three minutes. Real time PCR results were verified by electrophoresis of the reverse transcribed material in 1.2% agarose gels and visualized under UV illumination after ethidium bromide staining. Transcript quantities were compared to the amount of endogenous control (L7).

Generation of Stable Cardiac Cell Lines.

We developed a cell model to validate several of the predicted target genes. Double stable, miR-199b-inducible cells were generated using the T-REX system (Invitrogen) with modifications. Briefly, cells were transfected using FUGENE 6 reagent (Roche) with 8 µg pCAgβTrs-hygro, a vector expressing the Tet-repressor (TR) under control of a (3-actin promoter (generously provided by Hans Clevers, The Hubrecht Institute) and stable clones were selected with 250 µg/µl hygromycin. Selected colonies were transiently transfected with 0.2 µg pcDNA4/TO-luciferase (Invitrogen), using FUGENE 6 reagent (Roche), to test their responsiveness to doxycyclin (Dox) using the Dual Luciferase assay system (Promega). Two different Tet-repressor clones (TR1 and TR4), showing high luciferase activity and low background, were subsequently transfected with 8.5 µg pcDNA4/TO-miR-199b and cultured in the presence of hygromycin and 750 µg/µl of zeocin to generate double stable cell lines. Zeocin/hygromycin resistant clones were transiently transfected with a reporter construct encoding firefly luciferase under control of the proximal promoter region of the rat ANF gene (base pairs −3003 to +1 relative to the beginning of exon 1) to test their DOX-inducible miR-199b transcriptional activation profile. We selected two clones (TR1-2 and TR4-7), which systematically showed significant induction of miR-199b expression levels in the presence of doxycyclin in the culture media. In this way, we established a cellular system with inducible activation of miR-199b and concomitant translational repression of the endogenous miR-199b target genes (see FIG. 4).

Western Blot Analysis.

Proteins were extracted from clones TR1-2 and TR4-7, left untreated or treated with Dox, using cell lysis buffer (20 mM Tris pH 8.0, 150 mM NaCl, 1 mM EDTA, 1 mM EGTA, 1% Triton X-100) supplemented with a protease inhibitor cocktail (Complete Mini, Roche). SDS PAGE electrophoresis and blotting was performed as described in detail.[8] Antibodies used included rabbit polyclonal against Dyrk1A and mouse-monoclonal antibody to GAPDH (both from Santa Cruz), followed by corresponding horseradish peroxidase (HRP)-conjugated secondary antibodies (DAKO) and ECL detection.

Validation of Target Genes.

3' UTR regulatory sequences have been shown to be important for mRNA stability, translation, and transport. We designed primers specific for mouse sequences (http://ensembl.org) targeting the specific binding site of miR-199b on the 3'UTR of Dyrkl a (nucleotides 1536-1365, http://cbio.mskcc.org/cgi-bin/mirnaviewer/). After PCR amplification of this specific sequence, a PCR product with the expected size (286 bp) was visualized and isolated from a 1.2 agarose gel. After purification, the 3'UTR fragment was cloned into a pMIR-REPORT™ miRNA expression reporter vector (Ambion). This vector contains firefly luciferase under the control of the CMV mammalian promoter, with a miRNA target cloning region downstream of the luciferase translation sequence. This vector is optimized for cloning of miRNA targets and evaluation of miRNA regulation and, therefore, can be used as a screening tool to identify miRNA targets. After plasmid isolation and sequencing, the plasmid was used to transfect the double stable TR-miRl99b clones. Cells were cultured in 96-well plates, transfected with the pmiR-reporter-3'UTR Dyrk1a plasmid or the empty vector and incubated for 24 hours at 37° C. After one wash with PBS, cells were left untreated or were treated with Dox for 48 hours before measuring luciferase activity.

Statistical Analysis.

The results are presented as mean values±standard error of the mean (SEM). Statistical analyses were performed using Prism 5 software (GraphPad Software Inc.) and consisted of ANOVA followed by Turkey's post-test when group differences were detected at the 5% significance level, or Student's t-test when comparing two experimental groups.

Results

Differential Expression of Micrornas in Calcineurin Transgenic Mice.

Figure 2:
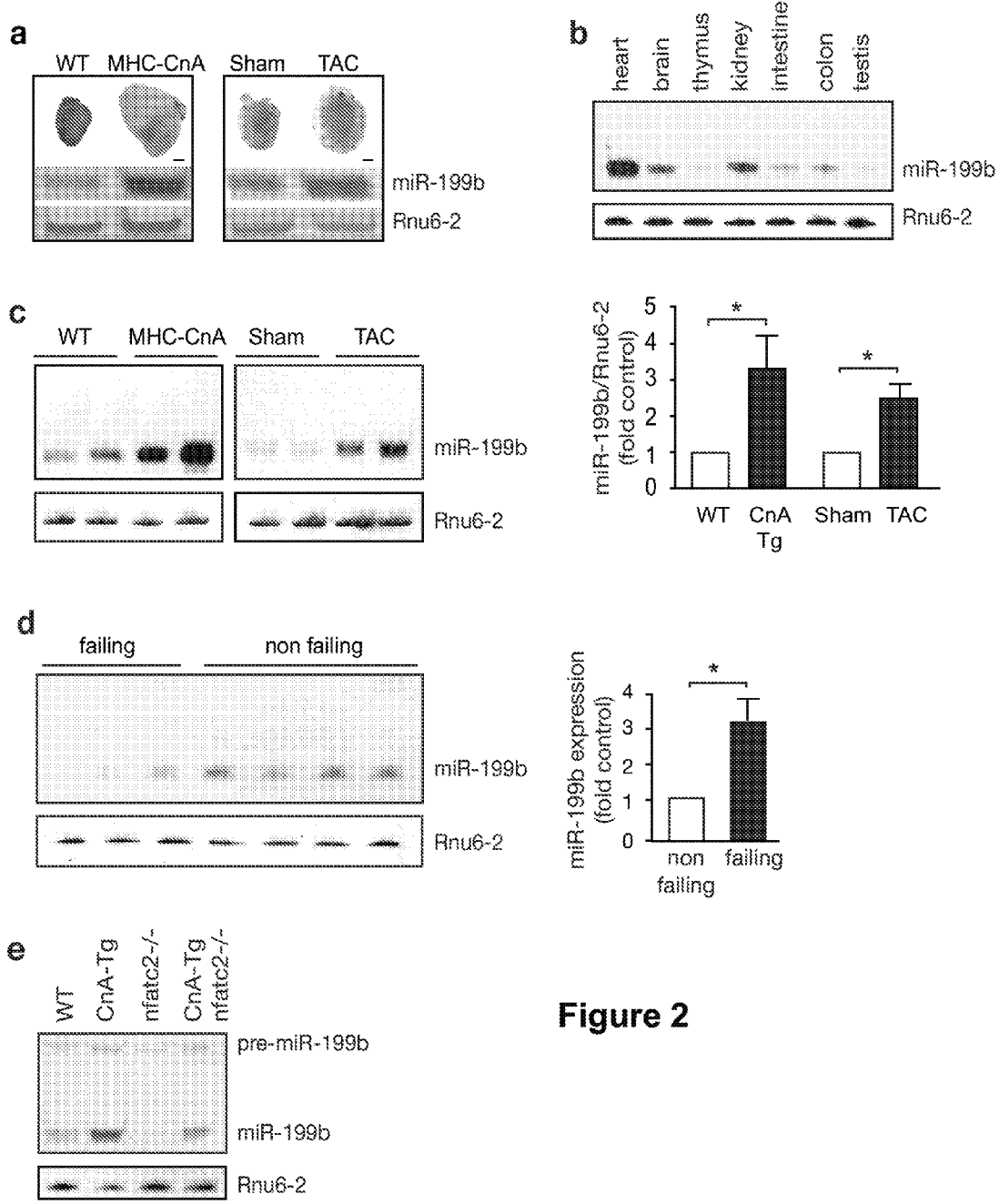
FIG. 2: MicroRNA-199b is up-regulated in calcineurin-induced cardiac hypertrophy. Panel a: Validation of the profiling array by Northern blotting analysis of miR-199b expression in cardiac tissue from αMHC-CnA transgenic mice and from mice subjected to TAC (Bar: 5 mm). Panel b: Expression pattern of miR-199b in different murine tissues analyzed by Northern blotting. Panel c: Northern blotting analysis of miR-199b expression in several hearts from αMHC-CnA transgenic mice and from mice subjected to TAC. Panel d: Northern blotting analysis of miR-199b in human biopsies of control and failing hearts. Panel e: miR-199b is up-regulated in hearts from αMHC-CnA transgenic mice, and reduced in hearts from knockout mice that lack NFATc2, suggesting that miR-199b is a direct calcineurin/NFAT target gene.

We profiled the expression levels of cardiac miRNAs in calcineurin transgenic mice. RNA was isolated from hearts of two-month-old wild-type and MHC-CnA transgenic mice and we performed miRNA profiling on these samples. The Hy3-labeled samples and a Hy5-labeled reference pool RNA sample were mixed pair-wise and hybridized to miRCURY LNA arrays, which contain capture probes targeting all miRNAs registered in the miRBASE version 8.1 at the Sanger Institute (345 miRNAs) and probes targeting licensed human sequences not yet annotated in miRBase (138 miRPlus, Exiqon). We detected microRNAs that are co-regulated with the development of calcineurin-induced heart failure using commercially available oligonucleotide microRNA microarrays (FIG. 1, Panel a), and we have analyzed the genomic localization of one specific microRNA: mmu-miR-199b and the human orthologue hsa-miR-199b (FIG. 1, Panel b). Human miR-199b is an intragenic microRNA encoded in the dynamin 1 (Dnm1) gene on the opposite strand in between exon 14 and 15 (FIG. 1, Panel b). Northern blot analysis of cardiac tissue isolated from MHC-CnA transgenic and transverse aortic constriction (TAC)-operated pressure overloaded mice, as two well established models of pathological cardiac hypertrophy, confirmed that miR-199b-5p is indeed strongly up-regulated in the diseased heart (FIG. 2, Panels a and c). Next, we analyzed its expression pattern in different murine tissues including heart, brain, thymus, kidney, intestine, colon and testis by Northern blotting (FIG. 2, Panel b). Although not cardiac specific, miR-199b-5p emerged as being highly abundant in the cardiac tissue. Further, miR-199b-5p is also more abundantly expressed in biopsies of human cardiac tissues of heart failure patients, compared to control, human healthy heart tissue (FIG. 2, Panel d). Finally, miR-199b is an immediate target gene of the calcineurin/NFAT pathways, since hearts from mice harboring a null allele of NFATc2 showed less miR-199b expression, both under baseline conditions as well as following chronic activation of calcineurin signaling (FIG. 2, Panel e).

Increased Expression of miR-199b in Cardiac Myocytes Induces Hypertrophy.

Figure 3:
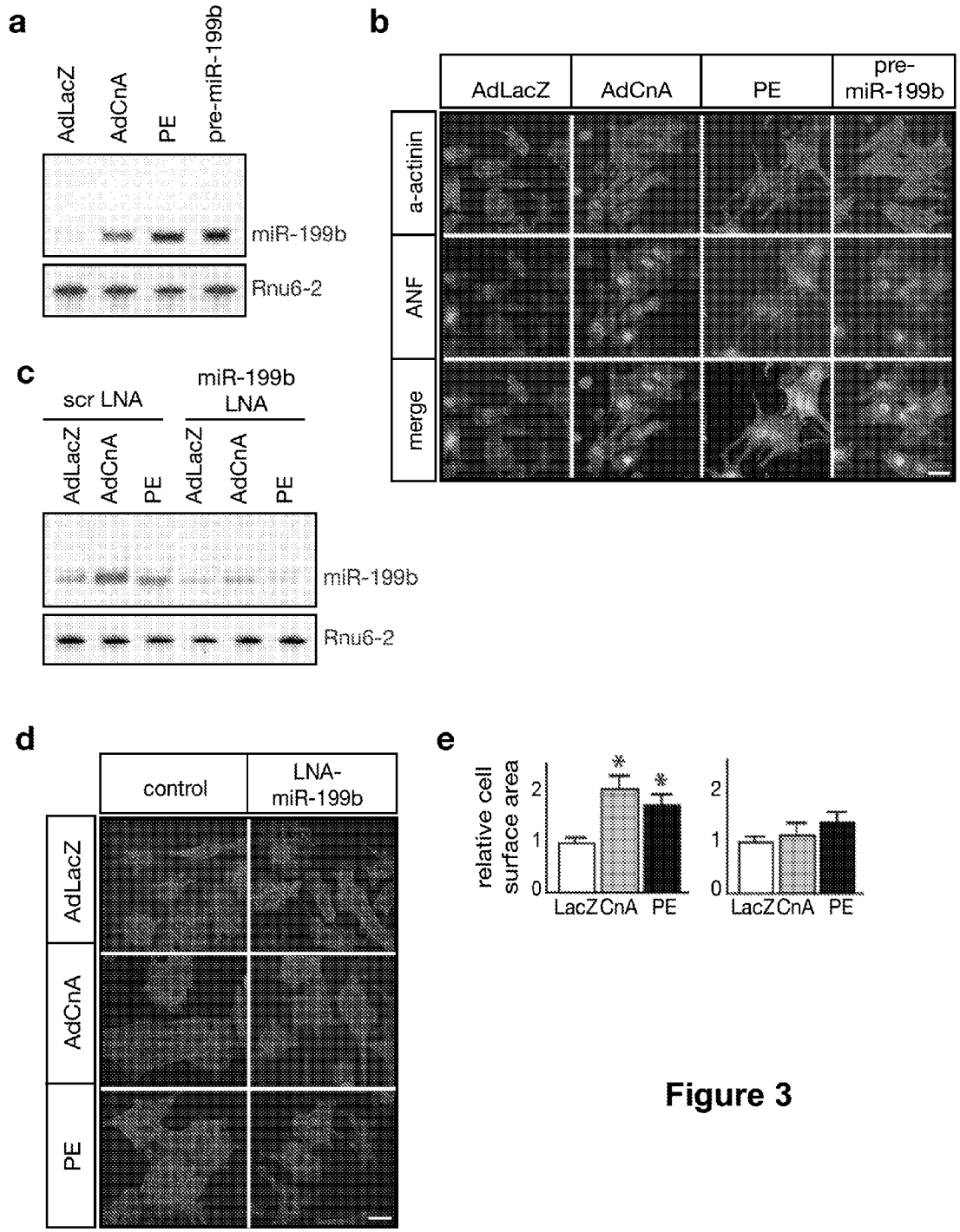
FIG. 3: Development of cardiomyocyte hypertrophy can be modulated by increased expression or inhibition of miR-199b. Panel a: Northern blot validation of miR-199b overexpression in neonatal rat cardiomyocytes by infection with an adenovirus expressing a constitutively activated form of calcineurin (AdCnA), stimulation with phenylephrine (PE), or transfection of a precursor molecule for miR-199b. Panel b: Representative confocal image of neonatal rat cardiomyocytes infected with a control adenovirus (AdLacZ), an adenovirus expressing active CnA (AdCnA) or treated with PE or a miR-199b precursor molecule. Cells were stained for a-actinin, ANF and a nuclear counterstain (TO-PRO-3). The data show dramatically enlarged cardiomyocytes with induction of perinuclear ANF upon overexpression of miR-199b, similar to known hypertrophic stimuli such as active calcineurin and PE. Panel c: Northern blot analysis of miR-199b expression in neonatal rat cardiomyocytes pretreated with a scrambled LNA probe or a miR-199b LNA probe, and infected with AdLacZ, AdCnA, or treated with PE. Panel d: Representative confocal image of neonatal rat cardiomyocytes pretreated with a control or miR-199b LNA probe and infected with AdLacZ, AdCnA, or treated with PE. Cells were stained for α-actinin and a nuclear counterstain (TO-PRO-3). Panel e: Quantification of cell surface areas under the indicated conditions confirms the rescue of the hypertrophic phenotype upon inhibition of miR-199b in cardiomyocytes. (Bar: 20 μm.)

To address the role of miR-199b in cardiomyocyte remodeling we transfected primary neonatal rat cardiomyocytes with miR-199b precursor molecules to overexpress miR-199b and compared them with cardiomyocyte cultures that have been infected with an adenovirus expressing LacZ, and adenovirus expressing an activated form of calcineurin (Ad-CnA), or that have been exposed to 10 mM phenylephrine (PE; FIG. 3, Panel a). To monitor the change in cell size or sarcomere organization induced by the different treatments, cardiomyocytes were stained for sarcomeric a-actinin (FIG. 3, Panel b). As expected, AdCnA or PE treatment resulted in robust hypertrophy response as shown by a significant increase in cell size and in perinuclear presence of ANF. Surprisingly, a similar increase in cell size and in ANF expression was observed in cardiomyocytes overexpressing miR-199b (FIG. 3, Panel b).

Inhibition of miR-199b Reduces Cardiomyocyte Hypertrophy.

To begin to assess the requirement of miR-199b downstream of (calcineurin-mediated) cardiomyocyte hypertrophy, we used antisense oligonucleotides targeting endogenous miR-199b (LNA-miR-199b), and transfected these oligonucleotides into primary cardiomyocyte cultures. As a control, cardiomyocytes were also transfected with a non-specific control oligonucleotide (FIG. 3, Panels c, d, and e). Next, we infected the cardiomyocyte cultures with an adenovirus expressing an activated form of calcineurin (AdCnA), or exposed to 10 mM phenylephrine (PE). To monitor the change in cell size or sarcomere organization, cardiomyocytes were stained for sarcomeric a-actinin. AdCnA or PE treatment resulted in a strong hypertrophic response when cells were treated with the control oligonucleotide. In contrast, pretreatment with the LNA-miR-199b completely abrogated the classical hypertrophy phenotype in response to AdCnA-infection or PE treatment (FIG. 3, Panel d). Quantification of the data indicated a two-fold increase in cell surface area in AdCnA-infected or PE-treated cells pretreated with the control oligonucleotide. These prohypertrophic effects of AdCnA and PE were abrogated by blocking the binding of miR-199b to its target mRNA (FIG. 3, Panel e).

MiR-199b is Predicted to Target Different Genes Downstream of the Calcineurin-NFAT Signaling Pathway.

Figure 4:
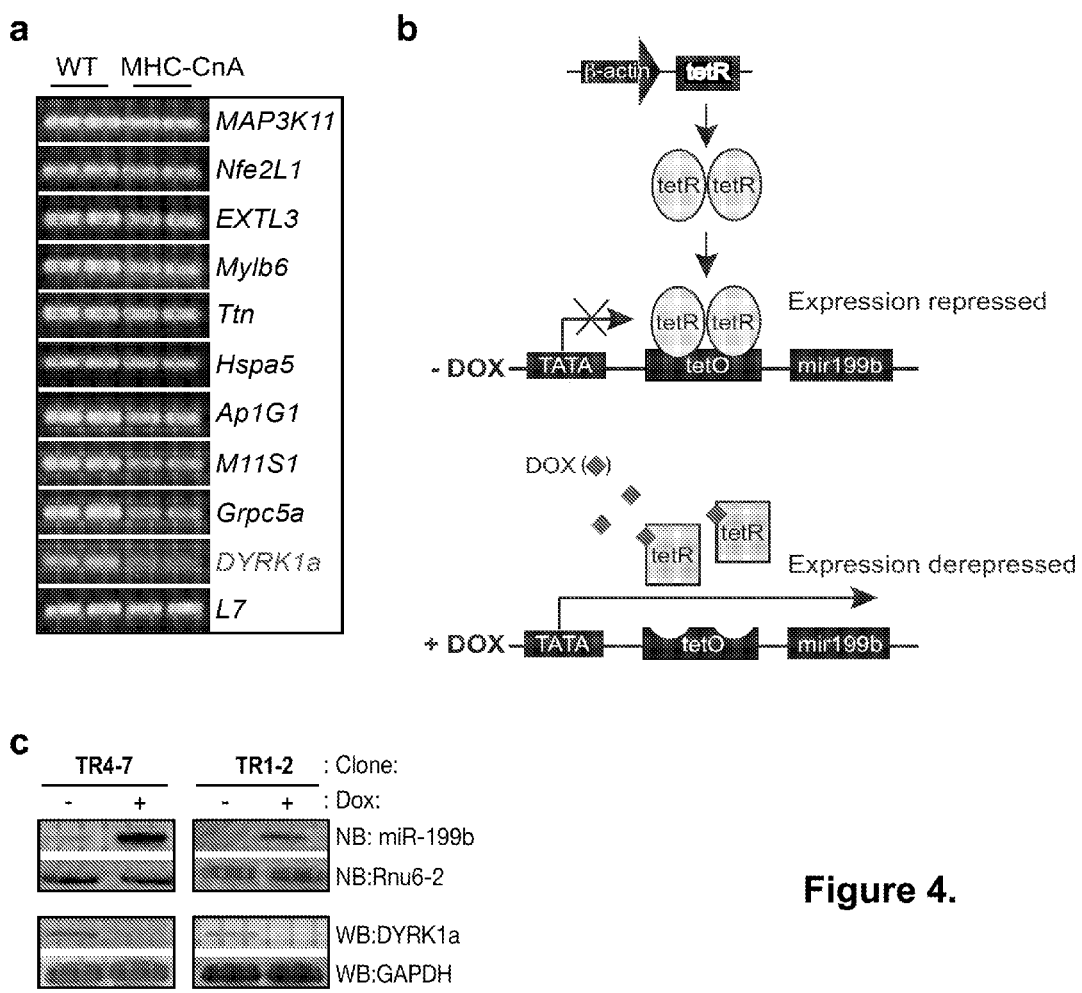
FIG. 4: MiR-199b is predicted to target Dyrk1a. Panel a: RNA from wild-type (non-transgenic) and MHC-CnA transgenic mice were analyzed by RT-PCR using primers designed against predicted target genes. The data show that although not all predicted genes showed altered expression in the MHC-CnA transgenic hearts, the expression of genes like Mylb6, M11S1, Grpc5a and Dyrk1a was clearly decreased. Panel b: Schematic representation of miR-199b expression manipulation by Dox on the double stable, miR-199b-inducible cells. Panel c: Northern blotting analysis of miR-199b expression in two miR-199b-inducible cell clones (TR4-7 and TR1-2), treated or not with DOX, clearly showing up-regulation of miR-199b by Dox-treatment. Protein levels of Dyrk1a (as a predicted target of miR-199b) were also determined in both clones by Western blotting analysis. The data clearly show that once miR-199b is up-regulated by Dox treatment, the protein levels of Dyrk1a dramatically decrease.

Despite the large number of identified miRNAs in several disease situations, only a handful of miRNAs have been functionally characterized. Complicated expression patterns and large numbers of predicted targets genes preclude a straight-forward analysis of their precise biological function. To understand the role of miR-199b in calcineurin-induced cardiac failure we undertook an expression analysis of predicted mmu-miR-199b mRNA targets listed in several public datasets developed based on several studies.[8-17] By RT-PCR we found that not all the predicted target mRNAs for miR-199b were differentially expressed in MHC-CnA transgenic hearts, compared to the wild-type hearts (FIG. 4, Panel a). However, genes like Mylb6, M11S1, Grpc5a, and, in particular, Dyrk1a were strongly down-regulated in MHC-CnA transgenic hearts. However, none of these genes, except for Dyrk1a, have been described to be linked to calcineurin/NFAT signaling pathway.

MiR-199b Overexpression Results in Down-Regulation of the Dual-Specificity Tyrosine-Phosphorylation Regulated Kinase, Dyrk1a.

From the genes that were down-regulated in MHC-CnA transgenic hearts at the transcript level, only Dyrk1a has been shown to be directly connected to this pathway. Recently, two independent groups obtained evidence linking dysregulation of NFAT signaling in Down's syndrome.[18-20] The NFAT family of transcription factors, which are critical to development, reside in the cytoplasm in a hyperphosphorylated form; they are dephosphorylated by calcineurin in response to calcium influx and translocate to the nucleus to activate target genes. Mice lacking various Nfatc genes showed abnormalities comparable to those of people with Down's syndrome. Examination of the region of human chromosome 21 believed to contain genes responsible for the Down syndrome phenotype revealed two potential regulators of NFAT signaling: DSCR1 (which encodes a calcineurin inhibitor) and DYRK1A (dual-specificity tyrosine-phosphorylation regulated kinase), which encodes a nuclear serine/threonine kinase. DYRK1A and DSCR1 synergistically inhibited NFAT-dependent transcription in cultured neurons. Moreover, DYRK1A was shown to phosphorylate NFAT and prime it for further phosphorylation by glycogen synthase kinase 3 (GSK3) and, therefore, to promote its export from the nucleus. Transgenic mice that overexpressed Dyrk1a and Dscr1 showed cardiovascular abnormalities most likely related to the cytoplasmic localization of endocardial NFAT. Based on these findings, we hypothesized that calcineurin/NFAT-dependent activation of miR-199b results in direct down-regulation of Dyrk1a expression. Being true, this would result in decreased phosphorylation of nuclear NFAT, decreased translocation of phosphorylated NFAT to cytoplasm and subsequent induction of the cardiac remodeling and hypertrophic response. To test this hypothesis we generated a cellular system with inducible activation of miR-199b (FIG. 4, Panel b) and, in theory, concomitant translational repression of the endogenous miR-199b target genes. Indeed, treatment of these cells with Dox showed an increase in miR-199b expression by Northern blotting analysis, in contrast with the untreated cells that expressed very low levels of the miR (FIG. 4, Panel c, NB). Correlated with an increase in miR-199b expression we observed a concomitant decrease in protein levels for Dyrk1a, showing that Dyrk1a is indeed a direct target of miR-199b (FIG. 4, Panel c, WB).

Dyrk1a is a Direct Target Gene of miR-199b.

Figure 5:
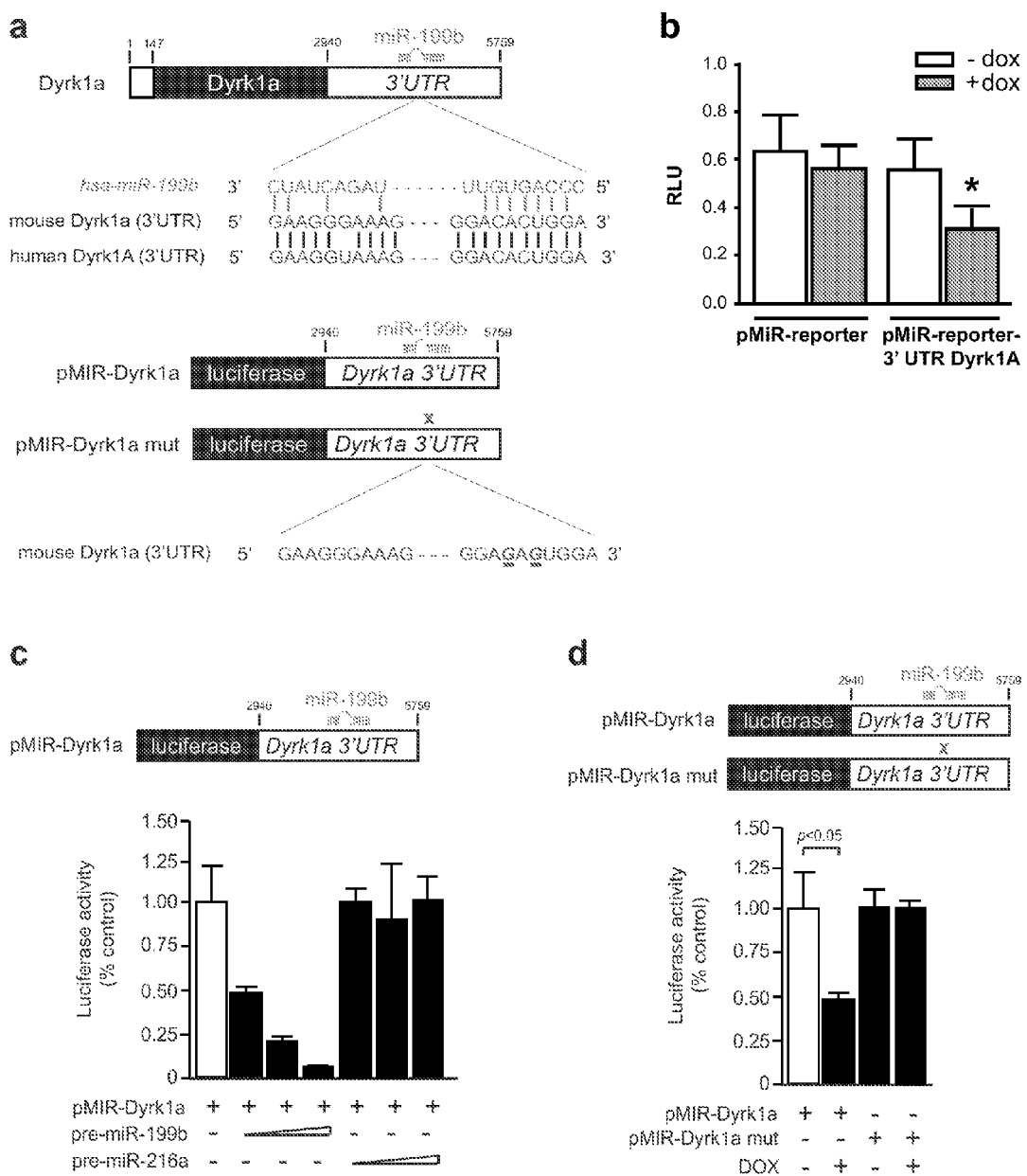
FIG. 5: Dyrk1a is a direct target gene of miR-199b. Panel a: Schematic representation of the 3'UTR of Dyrk1a showing the sequence where the seed region of miR-199b is predicted to bind. SEQ ID NOS: 6 and 7 are the depicted 3' and 5' ends of hsa-miR-199b, respectively. SEQ ID NOS: 8 and 9 are the depicted 5' and 3' end of mouse Dyrk1a (3'UTR), respectively. Schematic representation of the pMiR-reporter-3'UTR Dyrk1a. SEQ ID NOS: 8 and 12 are the depicted 5' and 3' ends of mouse Dyrk1a (3'UTR) therein, respectively. Panel b: MiR-199b-inducible clones were transfected with the pMiR-reporter-3'UTR Dyrk1a plasmid. Following DOX stimulation, luciferase activity is decreased. Panel c: HEK293 cells were co-transfected with increasing amounts of an expression vector with the precursor for miR-199b, resulting in a dose-dependent decrease in luciferase activity. In contrast, an expression vector with a precursor for an unrelated microRNA (miR-216a) has no effect on luciferase activity. Panel d: TR4-7 cells were left untreated or treated with Dox for 48 hours (to induce miR-199b expression) before measuring luciferase activity. The graph shows that upon overexpression of miR-199b (+Dox), the luciferase activity of the cells transfected with the pMiR-reporter-3'UTR Dyrk1a plasmid strongly decayed, indicating that miR-199b directly binds to the 3'UTR of Dyrk1a. In contrast, a mutated pMiR-reporter-3'UTR Dyrk1a did not react to Dox treatment, showing that the seed region in the 3'UTR of Dyrk1a is required for miR-199b-induced sensitivity.

To further analyze whether Dyrk1a is a direct target gene of miR-199b we looked more carefully at the 3'UTR sequence of Dyrk1a, more specifically to the miR-199b seed region. FIG. 5, Panel a, shows that this region is highly conserved between human (SEQ ID NOS:10 and 11) and mouse (SEQ ID NOS:8 and 9), suggesting that this is indeed a target sequence of miR-199b (SEQ ID NOS:6 and 7). To confirm this, we made use of a miRNA expression reporter vector (pMiR-reporter, Ambion). This vector contains firefly luciferase under the control of the CMV mammalian promoter. The 3' UTR of the luciferase gene contains a multiple cloning site for insertion of predicted miRNA binding targets or other nucleotide sequences. By cloning the sequence of the 3'UTR of Dyrk1a, to which miR199b is predicted to bind, into the pMiR-REPORT vector, the luciferase reporter will be subjected to regulation that will mimic regulation of the miRNA target (in this case, Dyrk1a; FIG. 5, Panel a). If overexpression of miR-199b would result in a decrease in luciferase activity, this would show that the 3'UTR sequence of Dyrk1a would be a direct target of this miR. Indeed, this is what we observed (FIG. 5, Panel b). In addition, we created a vector where we introduced two point mutations in the miR-199b seed region within the 3'UTR sequence of Dyrk1a as a control (SEQ ID NOS:8 and 12) (FIG. 5, Panel a). The p-MIR-reporter-3'UTR Dyrk1a was sensitive to miR-199b expression by expression of miR-199b upon DOX addition to inducible miR-199b expressing clones (FIG. 5, Panel b) and in a dose-dependent manner by transient co-transfection of a vector expressing miR-199b (FIG. 5, Panel c), while no sensitivity was observed for a co-expression of and unrelated microRNA, miR-216a (FIG. 5, Panel c). In addition, miR-199b-inducible clones treated or not with Dox for 48 hours were pre-transfected with the p-MiR-reporter-3'UTR Dyrk1a. Luciferase activity was strongly inhibited in the cells overexpressing miR-199b, compared to the cells left untreated or transfected with the empty vector, while a mutated p-MiR-reporter-3'UTR Dyrk1a showed no sensitivity to miR-199b expression (FIG. 5, Panel d). Combined, these data demonstrate the presence of a functional, and evolutionary conserved miR-199b seed region in the 3'UTR of Dyrk1a.

Antagomir-199b Rescues Calcineurin-Induced Heart Failure by Restoring Dyrk1a Expression Levels.

Figure 6:
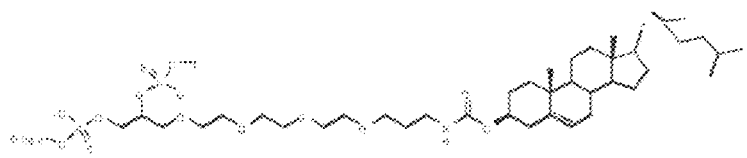
FIG. 6: Antagomir-199b treatment rescues calcineurin-induced cardiac hypertrophy in vivo by normalizing Dyrk1a expression. Panel a: Non-limiting example of a nucleotide sequence (SEQ ID NO:13) capable of inhibiting mir-199b (SEQ ID NO:2). Oligo description (antagomir): 20-23 nt long, all 2'-Ome, 3'-cholesterol modification of Type 1, 5-7 PS bonds, PAGE or HPLC purified. Panel b: Schematic representation of the treatment scheme, where two-week-old mice (calcineurin transgenic and wild-type littermates) were injected with antagomir to miR-199b (antagomir-199b) by daily intraperitoneal (IP) injections on three consecutive days. Panel c: Gross morphology of hearts isolated from vehicle or antagomir-199b-treated animals show a dramatic rescue of cardiac enlargement in calcineurin transgenic mice by antagomir-199b treatment. Panel d: Heart weight to body weight ratios confirm the rescue in heart size by antagomir-199b treatment in calcineurin transgenic mice. Panel e: Northern blot validation of the effectiveness of antagomir-199b treatment on depleting miR-199b expression in heart tissue from indicated treatment and genotypes. Panel f: Western blot analysis of Dyrk1a, showing down-regulation in vehicle-treated calcineurin transgenic mice, and normalization of Dyrk1a expression to wild-type levels by antagomir-199b treatment. Panel g: Normalization of NFAT activity in cardiac tissue by real time PCR analysis of the exon 4 splice isoform of RCAN1, a direct calcineurin/NFAT target gene.
Figure 6:
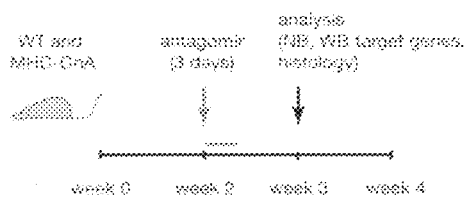
Figure 6:
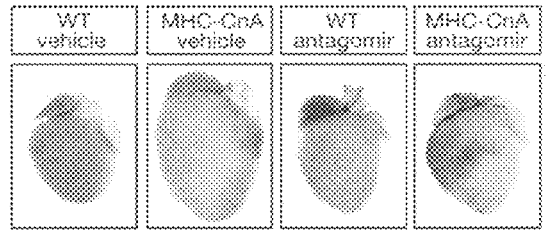
Figure 6:
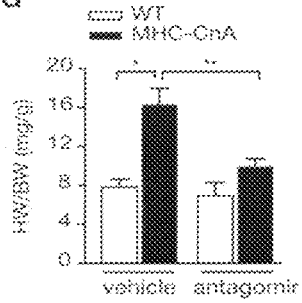
Figure 6:
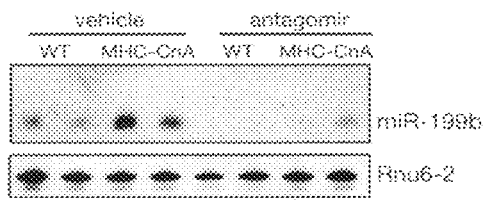
Figure 6:
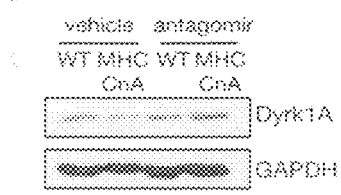
Figure 6:
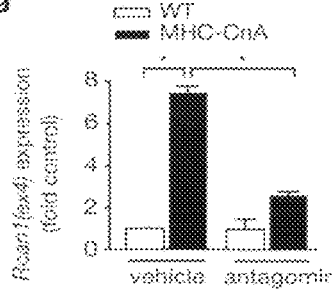

Finally, we made use of an antagomir approach designed to block endogenous miR-199b expression in vivo (FIG. 6, Panel a). To this end, we performed an experiment in which a chemically modified antisense oligonucleotide specific for miR-199b (antagomir-199b) was delivered by IP injection on three consecutive days to wild-type and calcineurin transgenic mice at the age of 14 days after birth (p 14; FIG. 6, Panel b). Mice tolerated antagomir-199b well without any obvious signs of illness or discomfort. Four days after the last injection we analyzed the gross morphology of the hearts, where we found calcineurin transgenic mice treated with antagomir-199b to have near normalized heart size (FIG. 6, Panels c and d) compared to vehicle-treated littermates. Northern blotting of cardiac tissue revealed a near completion of miR-199b expression in both wild-type and calcineurin transgenic mice, indicating the effectiveness of the antagomir-199b design (FIG. 6, Panel e). Interestingly, Dyrk1a expression levels were down-regulated to about 50% in vehicle-treated calcineurin transgenic mice compared to vehicle-treated wild-type mice (FIG. 6, Panel f). In contrast, antagomir-199b-treated animals demonstrated restored Dyrk1a protein levels. This was accompanied by normalized NFAT activity levels, as measured by the relative expression levels of RCAN1.4 transcript abundance (FIG. 6, Panel g).

Figure 7:
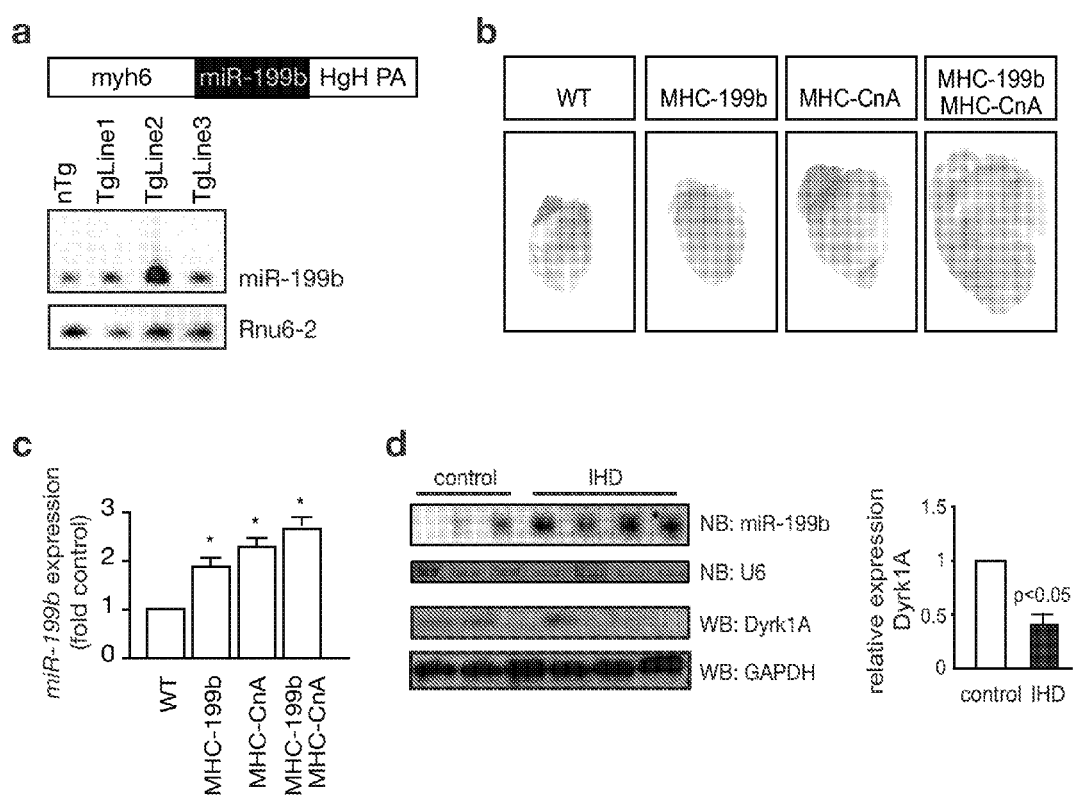
FIG. 7: Transgenic cardiac overexpression of miR-199b increases the susceptibility to heart failure signals. Panel a: Generation of transgenic mice overexpressing miR-199b in the post-natal myocardium under control of the alpha-myosin heavy chain promoter (MHC; above), and Northern blot analysis of miR-199b expression in three different transgenic lines. Panel b: The highest MHC-miR-199b overexpressor line was crossbred with calcineurin transgenic mice, resulting in a more dramatic cardiac enlargement in double transgenic mice compared to calcineurin transgenic mice alone. Panel c: Relative miR-199b expression levels in heart tissue from indicated groups. Panel d: miR-199b expression levels (Northern blots, top) inversely correlate with Dyrk1a protein expression (Western blots, below) in human heart tissue from control hearts and heart failure patients.

Conversely, we generated transgenic mouse lines overexpressing miR-199b in the post-natal myocardium using the alpha-myosin heavy chain promoter (FIG. 7, Panel a). We were able to generate three transgenic lines, each with differing overexpression of miR-199b as assessed by Northern blotting (FIG. 7, Panel a). At the age of three weeks, miR-199b overexpressors did not show an obvious cardiac phenotype. When we crossbred miR-199b transgenic mice with calcineurin transgenic mice, however, we observed a more exaggerated cardiac phenotype than mice only harboring the calcineurin transgene (FIG. 7, Panel b). The cardiac phenotype was reflected at the level of relative miR-199b expression level (FIG. 7, Panel c), as well as by relative heart weights. Finally, we also observed lowered Dyrk1a protein expression levels in biopsies of patients with ischemic heart failure, which correlated inversely with their expression of miR-199b (FIG. 7, Panel d).

All together, our data show for the first time that miR-199b plays an important role in calcineurin-induced cardiac hypertrophy. More importantly, we have identified the mechanism whereby miR-199b enhances calcineurin/NFAT-induced cardiomyocyte hypertrophy and, therefore, pathological cardiac hypertrophy, by active down-regulation of its direct target gene, Dyrk1a.

REFERENCES

1. Palermo J., J. Gulick, M. Colbert, J. Fewell, and J. Robbins. Transgenic remodeling of the contractile apparatus in the mammalian heart. *Circ. Res.* 1996; 78:504-509.
2. Molkentin J. D., J. R. Lu, C. L. Antos, B. Markham, J. Richardson, J. Robbins, S. R. Grant, and E. N. Olson. A calcineurin-dependent transcriptional pathway for cardiac hypertrophy. *Cell.* 1998; 93:215-228.
3. van Empel V. P., A. T. Bertrand, R. van der Nagel, S. Kostin, P. A. Doevendans, H. J. Crijns, E. de Wit, W. Sluiter, S. L. Ackerman, L. J. De Windt. Down-regulation of apoptosis-inducing factor in harlequin mutant mice sensitizes the myocardium to oxidative stress-related cell death and pressure overload-induced decompensation. *Circ. Res.* 2005; 96:e92-e101.
4. Schultz J. E., S. A. Witt, M. L. Nieman, P. J. Reiser, S. J. Engle, M. Zhou, S. A. Pawlowski, J. N. Lorenz, T. R. Kimball, and T. Doetschman. Fibroblast growth factor-2 mediates pressure-induced hypertrophic response. *J. Clin. Invest.* 1999; 104:709-719.
5. De Windt L. J., H. W. Lim, W. Taigen, D. Wencker, G. Condorelli, G. W. Dorn, 2nd, R. N. Kitsis, and J. D. Molkentin. Calcineurin-mediated hypertrophy protects cardiomyocytes from apoptosis in vitro and in vivo: An apoptosis-independent model of dilated heart failure. *Circ. Res.* 2000; 86:255-263.
6. He T. C., S. Zhou, L. T. da Costa, J. Yu, K. W. Kinzler, and B. Vogelstein. A simplified system for generating recombinant adenoviruses. *Proc. Natl. Acad. Sci. U.S.A.* 1998; 95:2509-2514.
7. Van Rooij E., P. A. Doevendans, C. C. De Theije, F. A. Babiker, J. D. Molkentin, L. J. De Windt. Requirement of nuclear factor of activated T-cells in calcineurin-mediated cardiomyocyte hypertrophy. *J. Biol. Chem.* 2002; 50:48617-48626.
8. Enright A. J., B. John, U. Gaul, T. Tuschl, C. Sander, and D. S. Marks. MicroRNA targets in Drosophila. *Genome Biol.* 2003; 5:R1.
9. John B., A. J. Enright, A. Aravin, T. Tuschl, C. Sander, D. S. Marks. Human MicroRNA targets. *PLoS Biol.* 2004; 2:e363.
10. Kiriakidou M., P. T. Nelson, A. Kouranov, P. Fitziev, C. Bouyioukos, Z. Mourelatos, and A. Hatzigeorgiou. A combined computational-experimental approach predicts human microRNA targets. *Genes Dev.* 2004; 18:1165-1178.
11. Krek A., D. Grun, M. N. Poy, R. Wolf, L. Rosenberg, E. J. Epstein, P. MacMenamin, P. I. da, K. C. Gunsalus, and M. Stoffel et al. Combinatorial microRNA target predictions. *Nat. Genet.* 2005; 37:495-500.

12. Lewis B. P., I. H. Shih, M. W. Jones-Rhoades, D. P. Bartel, C. B. Burge. Prediction of mammalian microRNA targets. *Cell.* 2003; 115:787-798.
13. Lewis B. P., C. B. Burge, and D. P. Bartel. Conserved seed pairing, often flanked by adenosines, indicates that thousands of human genes are microRNA targets. *Cell.* 2005; 120:15-20.
14. Rhoades M. W., B. J. Reinhart, L. P. Lim, C. B. Burge, B. Bartel, D. P. Bartel. Prediction of plant microRNA targets. *Cell.* 2002; 110:513-520.
15. Robins H., Y. Li, and R. W. Padgett. Incorporating structure to predict microRNA targets. *Proc. Natl. Acad. Sci. U.S.A.* 2005; 102:4006-4009.
16. Stark A., J. Brennecke, R. B. Russell, and S. M. Cohen. Identification of Drosophila MicroRNA targets. *PLoS Biol.* 2003; 1:E60.
17. Wang X. J., J. L. Reyes, N. H. Chua, T. Gaasterland. Prediction and identification of *Arabidopsis thaliana* microRNAs and their mRNA targets. *Genome Biol.* 2004; 5:R65.
18. Arron J. R., M. M. Winslow, A. Polleri, C-P Chang, H. Wu, X. Gao, J. R. Neilson, L. Chen, J. J. Heit, S. K. Kim, N. Yamasaki, T. Miyakawa, U. Francke, I. A. Graef, and G. R. Crabtree. NFAT dysregulation by increased dosage of DSCR1 and DYRK1A on chromosome 21. *Nature.* 2006; 441:595-600.
19. Gwack Y., S. Sharma, J. Nardone, B. Tanasa, A. Iuga, S. Srikanth, H. Okamura, S. Bolton, S. Feske, P. G. Hogan, and A. Rao. A genome-wide Drosophila RNAi screen identifies DYRK-family kinases as regulators of NFAT. *Nature.* 2006; 441:646-650.
20. Epstein C. J. Down's syndrome: Critical genes in a critical region. *Nature.* 2006; 441:582-583.

The invention claimed is:

1. A method for treating, diminishing, or delaying heart disease, the method comprising administering to an individual in need thereof a pharmaceutically effective amount of an inhibitor of microRNA miR-199b, wherein said inhibitor comprises a nucleic acid molecule that is complementary to said microRNA.

2. The method according to claim 1, wherein said inhibitor is capable of counteracting expression of microRNA miR-199b.

3. The method according to claim 1, wherein said inhibitor is capable of inhibiting or decreasing the expression of said microRNA in a cell.

4. The method according to claim 1, wherein said inhibitor of microRNA is capable of increasing or restoring the expression of Dyrk1a.

5. The method according to claim 1, wherein said inhibitor comprises an antisense nucleic acid molecule.

6. The method according to claim 1, wherein said inhibitor comprises:
    a nucleic acid sequence with a length of at least 20 nucleotides with at least 90% sequence identity to at least part of CCCAGUGUUUAGACUAUCUGUUC (hsa-miR-199b-5p) (SEQ ID NO:2) or the complement thereof, the part having at least 20 nucleotides, and/or
    a nucleic acid sequence with a length of at least 20 nucleotides with at least 90% sequence identity to at least a part of ACAGUAGUCUGCACAUUGGUUA (hsa-miR-199b-3p) (SEQ ID NO:3) or the complement thereof, the part having at least 20 nucleotides.

7. The method according to claim 1, wherein the nucleic acid comprises or encodes an inhibitor.

8. The method according to claim 1, wherein the nucleic acid sequence comprises a polynucleotide with a length of at least 18 nucleotides that is at least 90% complementary to at least 18 nucleotides of microRNA miR-199b.

9. A method for treating, diminishing, or delaying heart disease, the method comprising:
    providing a pharmaceutically effective amount of a vector to a subject in need thereof;
    wherein the vector comprises a nucleic acid comprising or encoding an inhibitor of the expression of the microRNA miR-199b.

10. The method according to claim 1, wherein said heart disease is associated with microRNA expression.

11. The method according to claim 1, wherein said heart disease is associated with decreased or inhibited expression of Dyrk1a.

12. The method according to claim 1, wherein said heart disease comprises hypertrophic heart disease and/or heart failure.

13. The method according to claim 1, wherein said heart disease is associated with a condition after heart-ischemia, diabetes and/or hypertension, and/or associated with at least one inherited genetic mutation that causes early- or late-onset congenital heart disease.

14. A method for treating, diminishing, or delaying a heart disease, the method comprising decreasing or inhibiting expression, amount and/or activity of miR-199b comprising administering a nucleic acid molecule that is complementary to mir-199b, thereby increasing or restoring the expression, amount and/or activity of Dyrk1a in a subject suffering from, or at risk of suffering from heart disease.

15. The method according to claim 9, wherein said heart disease is associated with microRNA expression.

16. The method according to claim 9, wherein said heart disease is associated with decreased or inhibited expression of Dyrk1a.

17. The method according to claim 9, wherein said heart disease comprises hypertrophic heart disease and/or heart failure.

18. The method according to claim 9, wherein said heart disease is associated with a condition after heart-ischemia, diabetes and/or hypertension, and/or associated with at least one inherited genetic mutation that causes early- or late-onset congenital heart disease.

19. The method according to claim 9, wherein the inhibitor comprises a nucleic acid molecule that is complementary to the microRNA.

20. The method according to claim 9, wherein the inhibitor is able to counteract expression of microRNA miR-199b.

21. The method according to claim 9, wherein the inhibitor is able to decrease or inhibit the expression of the microRNA in a cell.

22. The method according to claim 9, wherein the inhibitor of microRNA is able to increase or restore the expression of Dyrk1a.

23. The method according to claim 9, wherein the inhibitor comprises an antisense nucleic acid molecule.

24. The method according to claim 9, wherein the inhibitor comprises:
   a nucleic acid with a length of at least 20 nucleotides with at least 90% sequence identity to at least part of CCCAGUGUUUAGACUAUCUGUUC (hsa-miR-199b-5p) (SEQ ID NO:2) or the complement thereof, the part having at least 20 nucleotides, and/or
   a nucleic acid with a length of at least 20 nucleotides with at least 90% sequence identity to at least a part of ACAGUAGUCUGCACAUUGGUUA (hsa-miR-199b-3p) (SEQ ID NO:3) or the complement thereof, the part having at least 20 nucleotides.

25. The method according to claim 9, wherein the nucleic acid comprises or encodes an inhibitor.

26. The method according to claim 9, wherein the nucleic acid sequence comprises a polynucleotide with a length of at least 18 nucleotides that is at least 90% complementary to at least 18 nucleotides of microRNA miR-199b.

27. The method according to claim 9, wherein the vector comprises:
   a polynucleotide with a length of at least 20 nucleotides with at least 90% sequence identity to at least a part of CCCAGUGUUUAGACUAUCUGUUC (hsa-miR-199b-5p) (SEQ ID NO:2) or the complement thereof, the part having at least 20 nucleotides, and/or
   a polynucleotide with at least 90% sequence identity to at least a part of ACAGUAGUCUGCACAUUGGUUA (hsa-miR-199b-3p) (SEQ ID NO:3) or the complement thereof, the part having at least 20 nucleotides.

28. The method according to claim 9, wherein the vector is a retroviral, adenoviral, adeno-associated viral, or lentiviral vector.

29. The method according to claim 9, wherein the vector comprises a promoter suitable for expression in a mammalian cell, wherein the promoter is operably linked to a nucleic acid that, when expressed, is able to increase the expression, amount or activity of Dyrk1a.

30. The method according to claim 9, wherein the vector comprises a promoter suitable for expression in a mammalian cell, wherein the promoter is operably linked to a nucleic acid that, when expressed, is able to counteract the expression, amount and/or activity of a miR-199b microRNA.

31. The method according to claim 9, wherein the vector comprises a promoter suitable for expression in a heart muscle cell.

32. The method according to claim 9, wherein the nucleic acid comprises a polynucleotide with a length of at least 18 nucleotides that is at least 90% complementary to at least 20 nucleotides of microRNA miR-199b.

* * * * *

UNITED STATES PATENT AND TRADEMARK OFFICE
CERTIFICATE OF CORRECTION

PATENT NO.         : 8,383,603 B2                                          Page 1 of 1
APPLICATION NO.  : 12/737213
DATED              : February 26, 2013
INVENTOR(S)        : De Windt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 100 days.

Signed and Sealed this
First Day of September, 2015

Michelle K. Lee
*Director of the United States Patent and Trademark Office*

UNITED STATES PATENT AND TRADEMARK OFFICE
CERTIFICATE OF CORRECTION

PATENT NO.         : 8,383,603 B2
APPLICATION NO.    : 12/737213
DATED              : February 26, 2013
INVENTOR(S)        : Leon Johannes De Windt and Paula Alexandra Da Costa Martins It is certified that error appears in the above-identified patent and that said Letters Patent is hereby corrected as shown below:

In the specification:

COLUMN 15, LINE 45,    before --Schematic-- insert --SEQ ID NOS: 10 and 11 are the depicted 5' and 3' ends of human Dyrk1a (3'UTR), respectively.--

Signed and Sealed this
Fifteenth Day of December, 2015

Michelle K. Lee
*Director of the United States Patent and Trademark Office*